(12) United States Patent
Horiuchi et al.

(10) Patent No.: US 11,596,375 B2
(45) Date of Patent: *Mar. 7, 2023

(54) MAMMOGRAPHY APPARATUS

(71) Applicant: FUJIFILM Corporation, Tokyo (JP)

(72) Inventors: Hisatsugu Horiuchi, Kanagawa (JP); Yoshie Fujimoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 161 days.

This patent is subject to a terminal disclaimer.

(21) Appl. No.: 17/035,727

(22) Filed: Sep. 29, 2020

(65) Prior Publication Data

US 2021/0007693 A1   Jan. 14, 2021

Related U.S. Application Data

(63) Continuation of application No. 16/395,261, filed on Apr. 26, 2019, now Pat. No. 10,827,997.

(30) Foreign Application Priority Data

Apr. 27, 2018  (JP) .............................. JP2018-087170

(51) Int. Cl.
*A61B 6/00* (2006.01)
*A61B 6/04* (2006.01)

(52) U.S. Cl.
CPC ............ *A61B 6/502* (2013.01); *A61B 6/0414* (2013.01); *A61B 6/54* (2013.01)

(58) Field of Classification Search
CPC .......... A61B 6/502; A61B 6/0414; A61B 6/54
See application file for complete search history.

(56) References Cited

U.S. PATENT DOCUMENTS

| | | | | |
|---|---|---|---|---|
| 4,905,269 A | * | 2/1990 | Mosby | A61B 6/502 378/182 |
| 4,943,986 A | * | 7/1990 | Barbarisi | A61B 6/502 378/208 |
| 4,943,991 A | * | 7/1990 | Mosby | A61B 8/4281 378/185 |
| 5,029,193 A | * | 7/1991 | Saffer | A61B 6/502 378/208 |
| 5,083,305 A | * | 1/1992 | Tirelli | A61B 6/502 378/145 |
| 5,107,843 A | * | 4/1992 | Aarnio | A61B 6/502 600/461 |
| 5,199,056 A | * | 3/1993 | Darrah | A61B 6/502 378/208 |
| 5,506,877 A | * | 4/1996 | Niklason | A61B 6/502 378/208 |
| 5,541,972 A | * | 7/1996 | Anthony | A61B 6/0414 378/208 |

(Continued)

*Primary Examiner* — David P Porta
*Assistant Examiner* — Djura Malevic
(74) *Attorney, Agent, or Firm* — JCIPRNET

(57) ABSTRACT

The mammography apparatus includes an imaging stand that includes a recess that cuts out at least a part of a contact face that comes in contact with a chest wall of a subject, in which the recess has a shape in which between a first ridge portion where the contact face and an upper face are connected to each other, and a second ridge portion where the contact face and a lower face are connected to each other, at least a part of the second ridge portion is cut out, and the first ridge portion is not cut out.

15 Claims, 14 Drawing Sheets

(56) References Cited

U.S. PATENT DOCUMENTS

| | | | | |
|---|---|---|---|---|
| 5,664,573 A * | 9/1997 | Shmulewitz | A61B 6/4291 | 128/915 |
| 5,851,180 A * | 12/1998 | Crosby | A61B 6/502 | 600/407 |
| 6,064,715 A * | 5/2000 | Sklebitz | A61B 6/4233 | 378/98.3 |
| 6,507,748 B2 * | 1/2003 | Selland | A61B 6/502 | 600/407 |
| 6,560,480 B1 * | 5/2003 | Nachaliel | A61B 5/6848 | 600/547 |
| 6,577,702 B1 * | 6/2003 | Lebovic | A61B 6/502 | 378/68 |
| 6,647,089 B1 * | 11/2003 | Virta | A61B 6/502 | 378/37 |
| 6,741,673 B2 * | 5/2004 | Kamenetsky | A61B 6/502 | 378/208 |
| 6,968,033 B2 * | 11/2005 | Lebovic | A61B 6/04 | 378/68 |
| 7,085,346 B1 * | 8/2006 | Virta | A61B 6/4283 | 378/172 |
| D540,949 S * | 4/2007 | Sundstrom | D24/183 | |
| 7,440,539 B2 * | 10/2008 | Danielsson | A61B 6/502 | 378/150 |
| 7,505,555 B2 * | 3/2009 | Hermann | A61B 6/502 | 378/210 |
| D597,210 S * | 7/2009 | Hirabayashi | D24/158 | |
| 7,656,993 B2 * | 2/2010 | Hoernig | A61B 6/0414 | 128/845 |
| D625,011 S * | 10/2010 | Hirabayashi | D24/158 | |
| 7,876,876 B2 * | 1/2011 | Ohta | A61B 6/0414 | 378/37 |
| 7,963,918 B2 * | 6/2011 | Park | A61B 8/4209 | 600/407 |
| D731,656 S * | 6/2015 | Baxley | D24/158 | |
| 9,782,135 B2 * | 10/2017 | Stango | A61B 6/502 | |
| 9,895,132 B2 * | 2/2018 | Matsuura | A61B 6/502 | |
| 9,949,719 B2 * | 4/2018 | Zhang | A61B 8/4416 | |
| 10,219,757 B2 * | 3/2019 | Nakayama | A61B 6/0414 | |
| 10,463,319 B2 * | 11/2019 | Kobayashi | A61B 6/4488 | |
| 10,588,600 B2 * | 3/2020 | Arai | A61B 6/0414 | |
| 10,827,997 B2 * | 11/2020 | Horiuchi | A61B 6/54 | |
| 10,888,292 B2 * | 1/2021 | Stango | A61B 6/0414 | |
| 11,064,956 B2 * | 7/2021 | Defreitas | A61B 6/0485 | |
| 11,259,759 B2 * | 3/2022 | Stango | A61B 6/04 | |
| 2001/0053880 A1 * | 12/2001 | Selland | A61B 6/0414 | 600/407 |
| 2003/0007597 A1 * | 1/2003 | Higgins | A61B 6/0414 | 378/37 |
| 2003/0099325 A1 * | 5/2003 | Galkin | A61B 6/502 | 378/37 |
| 2003/0174807 A1 * | 9/2003 | Lebovic | A61B 6/0414 | 378/37 |
| 2005/0008117 A1 * | 1/2005 | Livingston | A61B 6/0414 | 378/37 |
| 2005/0063509 A1 * | 3/2005 | Defreitas | A61B 6/502 | 378/37 |
| 2006/0050844 A1 * | 3/2006 | Galkin | A61B 6/4283 | 378/37 |
| 2006/0126794 A1 * | 6/2006 | Hermann | A61B 6/0414 | 378/180 |
| 2006/0245541 A1 * | 11/2006 | Aubel | A61B 6/0414 | 378/37 |
| 2007/0058774 A1 * | 3/2007 | Ramsauer | A61B 6/502 | 378/37 |
| 2008/0112534 A1 * | 5/2008 | Defreitas | A61B 6/502 | 378/37 |
| 2008/0247508 A1 * | 10/2008 | Harrington | A61B 6/045 | 219/217 |
| 2009/0003519 A1 * | 1/2009 | Defreitas | A61B 6/025 | 378/37 |
| 2009/0080605 A1 * | 3/2009 | Miyako | A61B 6/0414 | 250/370.15 |
| 2009/0086928 A1 * | 4/2009 | Nakata | A61B 6/0414 | 378/209 |
| 2009/0145893 A1 * | 6/2009 | Harrington | A61B 6/045 | 219/494 |
| 2009/0220055 A1 * | 9/2009 | Nakata | A61B 6/502 | 378/208 |
| 2009/0323892 A1 * | 12/2009 | Hitzke | A61B 6/502 | 378/37 |
| 2010/0208037 A1 * | 8/2010 | Sendai | A61B 6/463 | 348/51 |
| 2011/0087132 A1 * | 4/2011 | DeFreitas | A61B 90/17 | 378/62 |
| 2011/0242092 A1 * | 10/2011 | Kashiwagi | A61B 6/502 | 345/419 |
| 2012/0114095 A1 * | 5/2012 | Smith | A61B 6/4441 | 378/20 |
| 2013/0051520 A1 * | 2/2013 | Ramsauer | A61B 6/025 | 378/37 |
| 2013/0138016 A1 * | 5/2013 | Shekhara | A61B 6/502 | 600/587 |
| 2013/0272493 A1 * | 10/2013 | Otokuni | A61B 6/4266 | 378/37 |
| 2013/0281840 A1 * | 10/2013 | Vaughan | A61B 6/4417 | 600/425 |
| 2014/0093033 A1 * | 4/2014 | Takata | A61B 6/04 | 378/208 |
| 2014/0093034 A1 * | 4/2014 | Takata | A61B 6/0414 | 378/208 |
| 2014/0177791 A1 * | 6/2014 | Otokuni | A61B 6/04 | 378/208 |
| 2015/0265186 A1 * | 9/2015 | Kuwabara | A61B 5/708 | 378/37 |
| 2015/0282770 A1 * | 10/2015 | Klanian | A61B 6/0414 | 378/208 |
| 2015/0302615 A1 * | 10/2015 | Fukuda | A61B 6/502 | 378/19 |
| 2016/0081633 A1 * | 3/2016 | Stango | A61B 6/025 | 378/37 |
| 2016/0166234 A1 * | 6/2016 | Zhang | A61B 6/502 | 600/443 |
| 2016/0183889 A1 * | 6/2016 | Matsuura | A61B 6/54 | 378/37 |
| 2016/0242709 A1 * | 8/2016 | Radicke | A61B 6/547 | |
| 2016/0249868 A1 * | 9/2016 | Nakayama | A61B 6/4233 | 378/4 |
| 2016/0256119 A1 * | 9/2016 | Nakayama | A61B 6/541 | |
| 2016/0256125 A1 * | 9/2016 | Smith | A61B 6/0414 | |
| 2017/0281124 A1 * | 10/2017 | Arai | A61B 8/403 | |
| 2018/0110484 A1 * | 4/2018 | Kobayashi | A61B 6/502 | |
| 2018/0125437 A1 * | 5/2018 | Stango | A61B 6/04 | |
| 2018/0368796 A1 * | 12/2018 | Hoernig | A61B 6/502 | |
| 2020/0069274 A1 * | 3/2020 | Stango | A61B 6/04 | |
| 2020/0146652 A1 * | 5/2020 | Arai | A61B 6/0414 | |
| 2020/0359975 A1 * | 11/2020 | Banks | A61B 6/0435 | |

* cited by examiner

MAMMOGRAPHY APPARATUS

CROSS-REFERENCE TO RELATED APPLICATIONS

This is a continuation application of and claims the priority benefit of a prior application Ser. No. 16/395,261 filed on Apr. 26, 2019, now allowed. The prior application Ser. No. 16/395,261 claims priority under 35 U.S.C § 119(a) to Japanese Patent Application No. 2018-087170 filed on 27 Apr. 2018. Each of the above application(s) is hereby expressly incorporated by reference, in its entirety, into the present application.

BACKGROUND OF THE INVENTION

1. Field of the Invention

The present invention relates to a mammography apparatus that images a breast using X-rays.

2. Description of the Related Art

In craniocaudal imaging (so-called CC imaging), in order to avoid physical interference with an abdomen of a subject, a mammography apparatus in which an imaging stand is formed to be thin on a subject side thereof is known (JP1999-070107A (JP-H11-070107A), corresponding to U.S. Pat. No. 6,064,715A). Further, a mammography apparatus having a structure in which a portion of an imaging stand that is in contact with a subject is generally bent in a height direction between an upper face and a lower face is known (JP2004-154409A).

SUMMARY OF THE INVENTION

In breast cancer screening, craniocaudal imaging (so-called CC imaging) and mediolateral oblique imaging (so-called MLO imaging) are performed. In the CC imaging, there is a case where an abdomen of a subject physically interferes with an imaging stand and thus the imaging stand does not easily come in contact with a chest wall. In this case, in a case where the imaging stand is excessively pushed to the subject in order to image the breast up to the vicinity of the chest wall, the abdomen of the subject is pressurized, and thus, large stress is applied to the subject. For example, such a related-art mammography apparatus having a shape that a contact face that is in contact with the chest wall of the subject is generally bent in the height direction between the upper face and the lower face can reduce the stress applied to the subject whose the chest wall or the abdomen is pressurized in the CC imaging, but since an X-ray imaging panel should be disposed on an inner side (a side distant from the subject) of the bent contact face, there is a disadvantage in that it is difficult to image the breast (a root portion of the breast) in the vicinity of the chest wall.

Further, in the MLO imaging, the imaging is performed in a state where an imaging stand is tilted (for example, in a state where the imaging stand is tilted in a longitudinal direction), but in a case where the subject cannot put an arm on a side face of the imaging stand, the stress applied to the subject becomes large.

An object of the invention is to provide a mammography apparatus capable of reducing stress applied to a subject in CC imaging, easily imaging a breast up to the vicinity of a chest wall compared with a related-art mammography apparatus having a shape that a contact face is generally bent in a height direction between an upper face and a lower face, and reducing stress applied to a subject in MLO imaging compared with a related-art mammography apparatus in which it is difficult to put an arm on a side face of an imaging stand.

According to an aspect of the invention, there is provided a mammography apparatus comprising: an X-ray irradiation section that irradiates an X-ray imaging panel with X-rays; and an imaging stand that includes the X-ray imaging panel and a control circuit of the X-ray imaging panel, and is provided with an upper face on which a breast of a subject is placed, a lower face that is opposite to the upper face, a contact face that is connected to the upper face and the lower face and comes in contact with a chest wall of the subject, a first side face and a second side face that are connected to the upper face, the lower face, and the contact face, and a recess formed by cutting out at least a part of the contact face, wherein the recess has a shape in which among a first ridge portion where the contact face and the upper face are connected to each other, a second ridge portion where the contact face and the lower face are connected to each other, a third ridge portion where the contact face and the first side face are connected to each other, and a fourth ridge portion where the contact face and the second side face are connected to each other, at least a part of the second ridge portion is cut out, and the first ridge portion, the third ridge portion, and the fourth ridge portion are not cut out.

It is preferable that the recess is present in a part of the second ridge portion including a center of the second ridge portion.

It is preferable that the recess has a structure in which the second ridge portion is chamfered.

It is preferable that the recess is formed in a curved surface that is convex toward the upper face.

It is preferable that a top of a boundary line between the recess and the contact face is disposed at the center between the first side face and the second side face, when seen from the contact face.

It is preferable that the recess is disposed on the lower face side of the X-ray imaging panel, when seen from the contact face.

It is preferable that a first control circuit disposed on the lower face side and the first side face of the X-ray imaging panel and a second control circuit disposed on the lower face side and the second side face side of the X-ray imaging panel are provided as the control circuit, and the recess is disposed between the first control circuit and the second control circuit, when seen from the contact face.

It is preferable that the control circuit is disposed on the lower face side of the X-ray imaging panel, and the recess is convex toward the upper face further than the control circuit, when seen from the contact face.

It is preferable that a point of the recess that is the closest to the upper face side is disposed on the upper face side further than a line that passes through a point of the control circuit that is the closest to the lower face side and is parallel to the upper face, when seen from the contact face.

It is preferable that a point of the recess that is the closest to the upper face side is disposed between a line that passes through a point of the control circuit that is the closest to the lower face side and is parallel to the upper face and a line that passes through a point of the control circuit that is the closest to the upper face side and is parallel to the upper face, when seen from the contact face.

It is preferable that the control circuit is disposed on the lower face side of the X-ray imaging panel, and the control circuit is disposed so that an edge portion thereof on the side of the recess is tilted toward the upper face, when seen from the contact face.

It is preferable that the first side face and the second side face include a straight portion that crosses the contact face at 90 degrees, in at least a specific range from the contact face.

It is preferable that the recess in the contact face has a length that is equal to or larger than 15% of the X-ray imaging panel.

According to the aspects of the invention, it is possible to provide a mammography apparatus capable of reducing stress applied to a subject in CC imaging, easily imaging a breast up to the vicinity of a chest wall compared with a related-art mammography apparatus having a shape that a contact face is generally bent in a height direction between an upper face and a lower face, and reducing stress applied to a subject in MLO imaging compared with a related-art mammography apparatus in which it is difficult to put an arm on a side face of an imaging stand.

Figure 2:
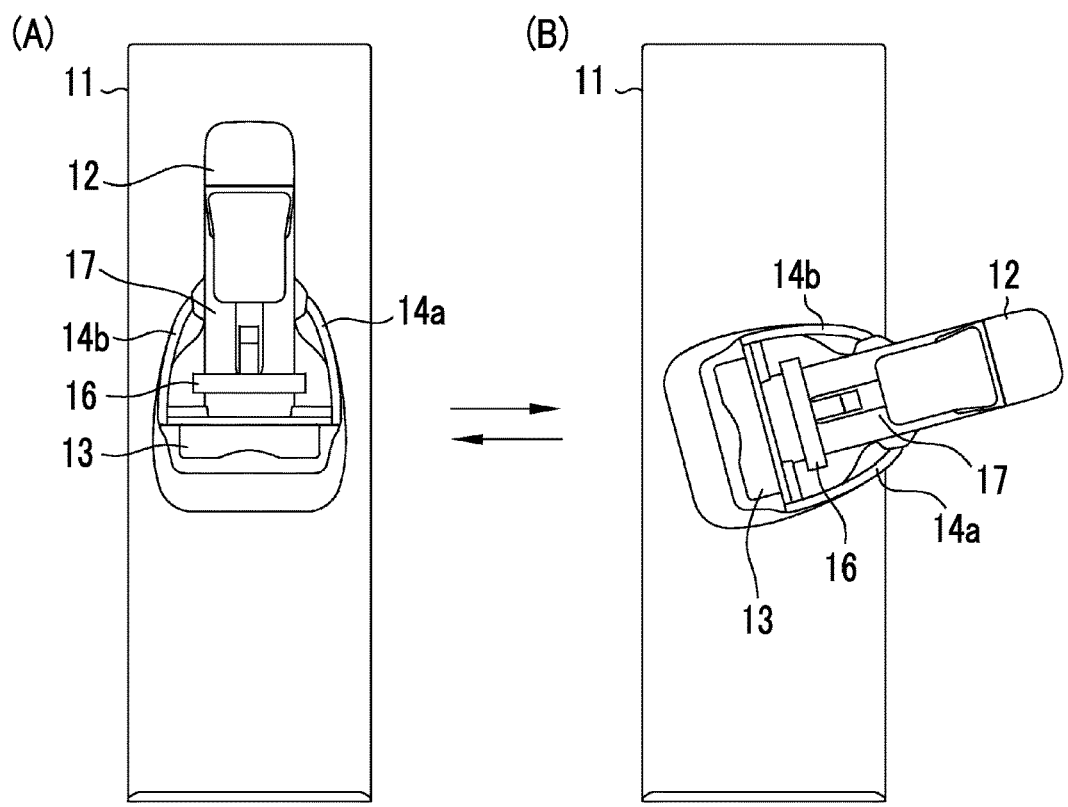

(A) of FIG. 2 is a diagram illustrating a direction of an X-ray imaging unit in CC imaging, and (B) of FIG. 2 is a diagram illustrating a direction of the X-ray imaging unit in MLO imaging.

Figure 3:
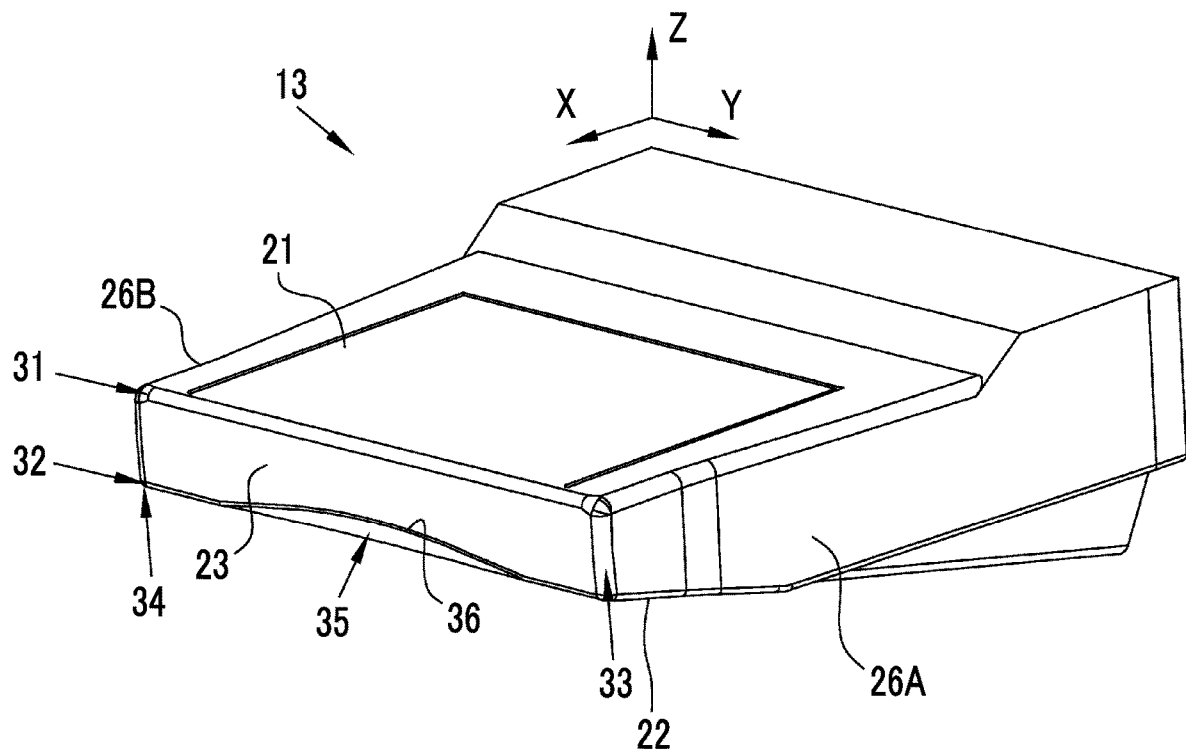

FIG. 3 is a perspective view of an imaging stand.

Figure 4:
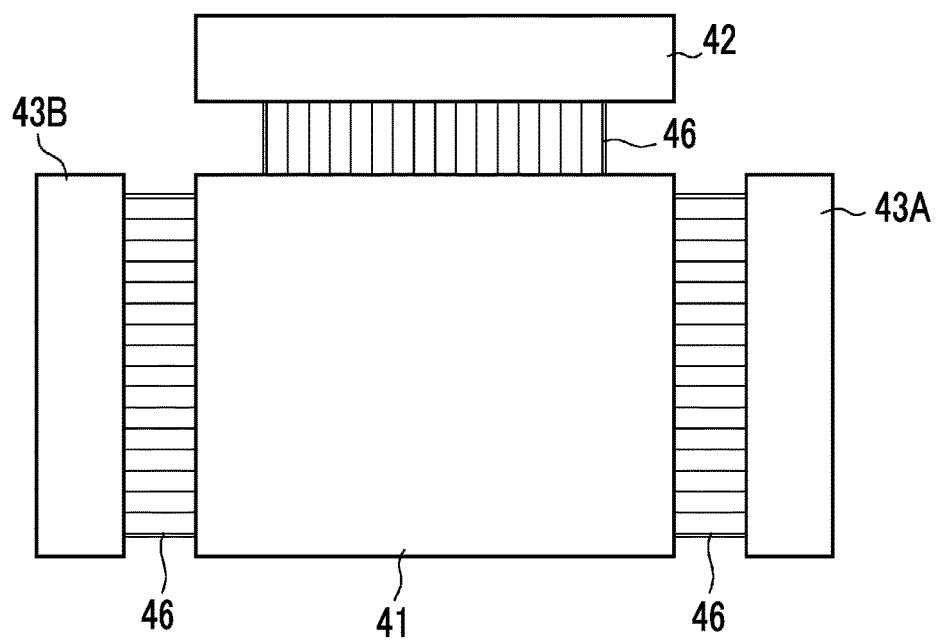

FIG. 4 is a diagram illustrating an X-ray imaging panel or the like provided inside the imaging stand.

Figure 5:
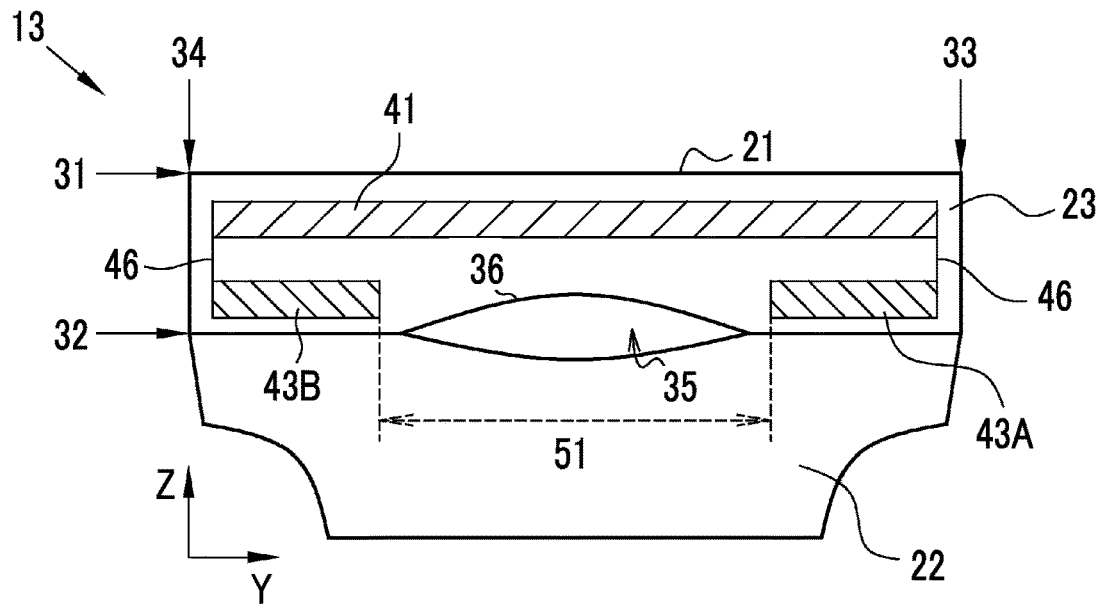

FIG. 5 is a diagram illustrating a positional relationship between an X-ray imaging panel or the like and a recess.

Figure 6:
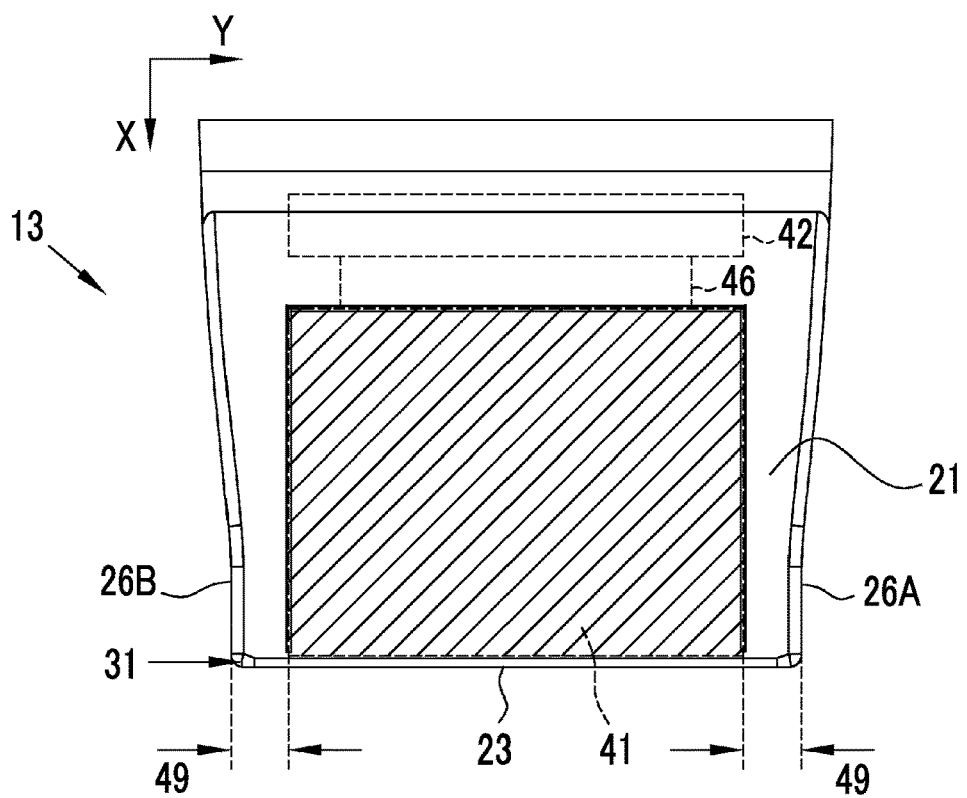

FIG. 6 is a diagram illustrating a disposition of an X-ray imaging panel or the like in the imaging stand.

Figure 7:
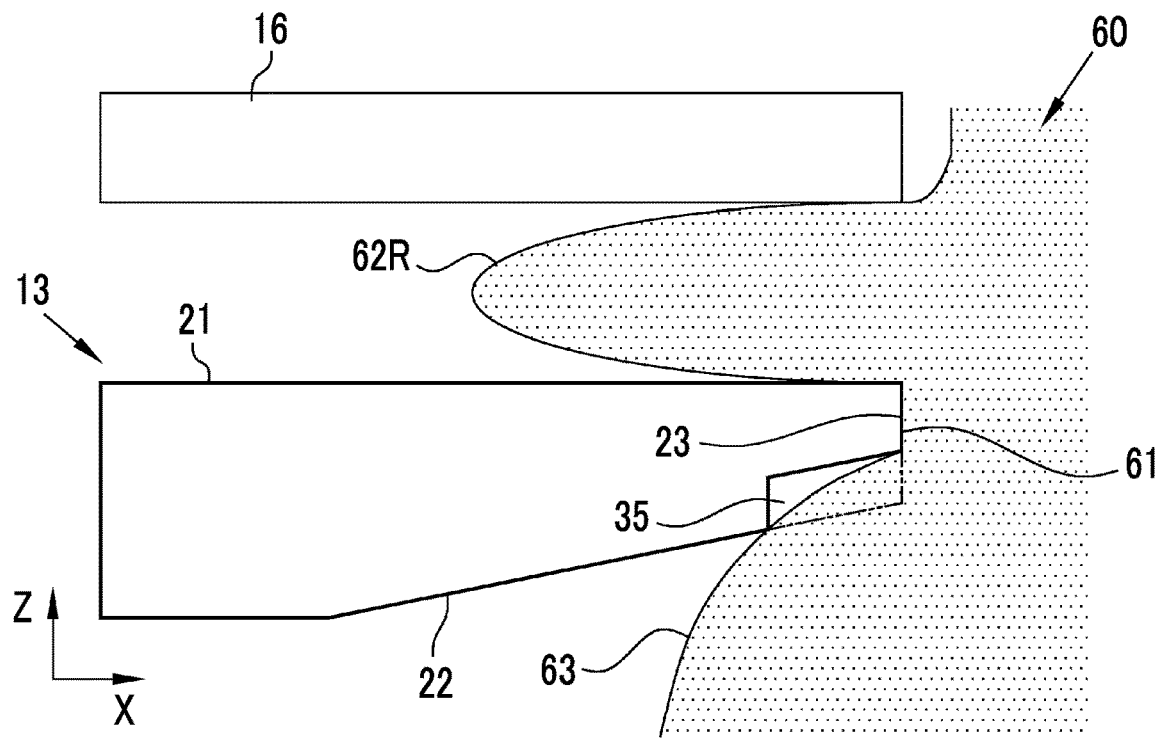

FIG. 7 is a diagram illustrating a disposition of the imaging stand in CC imaging.

Figure 8:
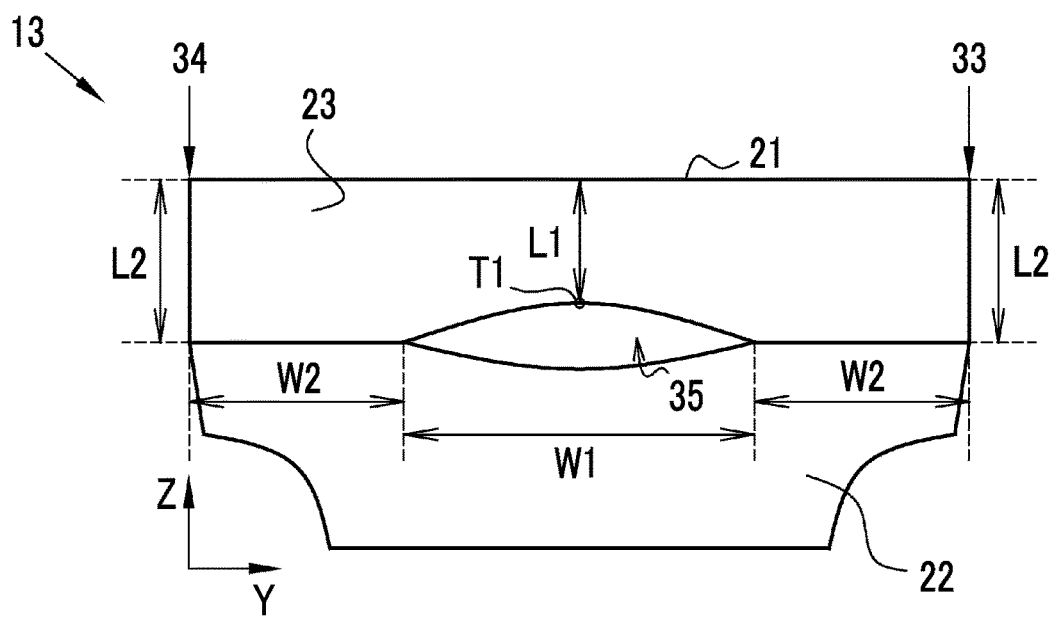

FIG. 8 is a diagram illustrating balance of lengths in the imaging stand.

Figure 9:
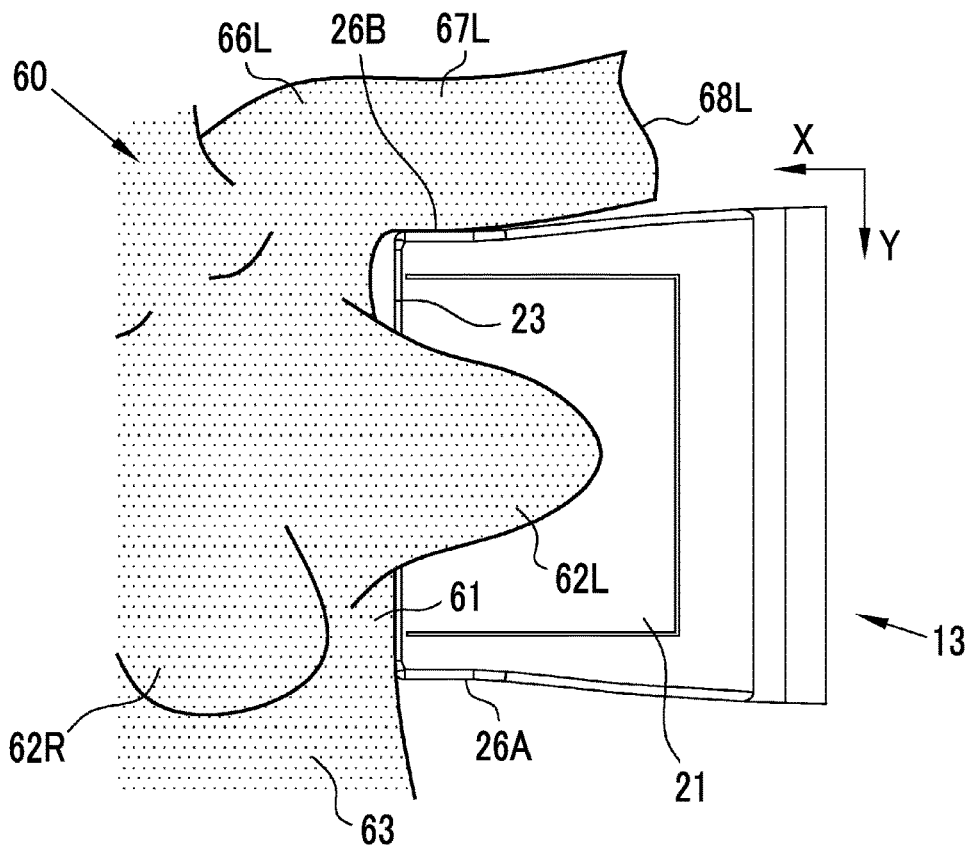

FIG. 9 is a diagram illustrating a disposition of the imaging stand in MLO imaging.

Figure 10:
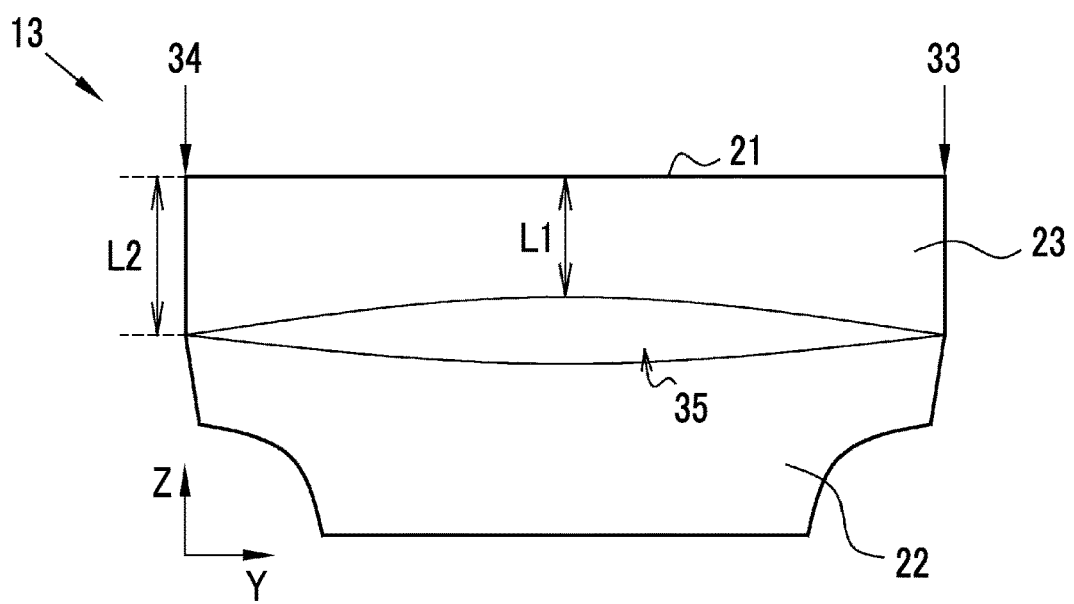

FIG. 10 is a diagram illustrating a modification example in which the recess is formed in an overall region of a second ridge portion.

Figure 11:
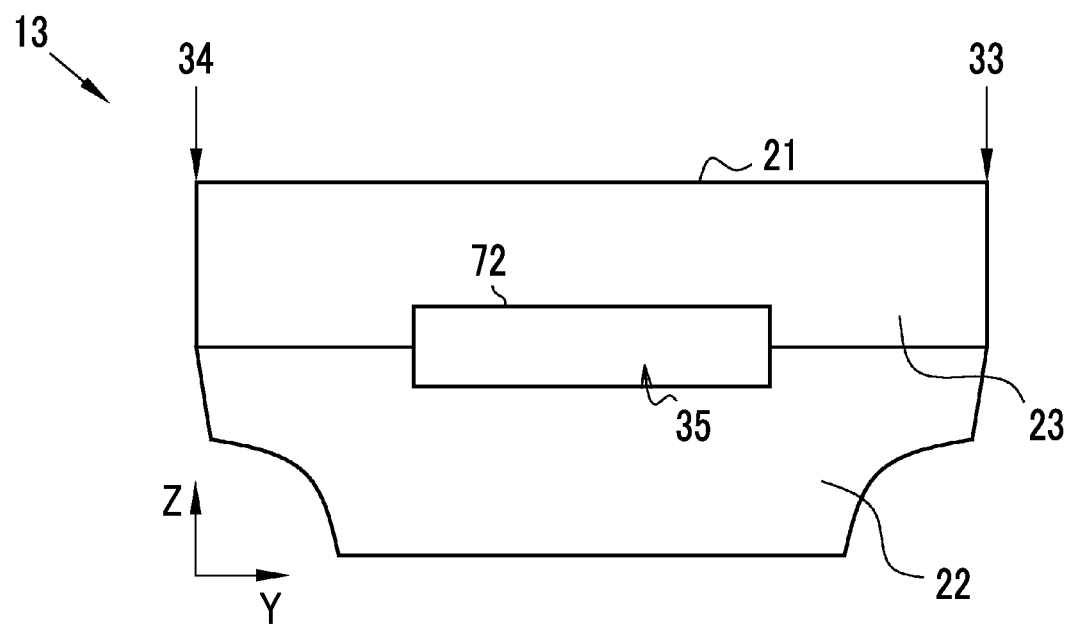

FIG. 11 is a diagram illustrating a modification example in which an outer periphery of the recess on a contact face is formed in a rectangular shape.

Figure 12:
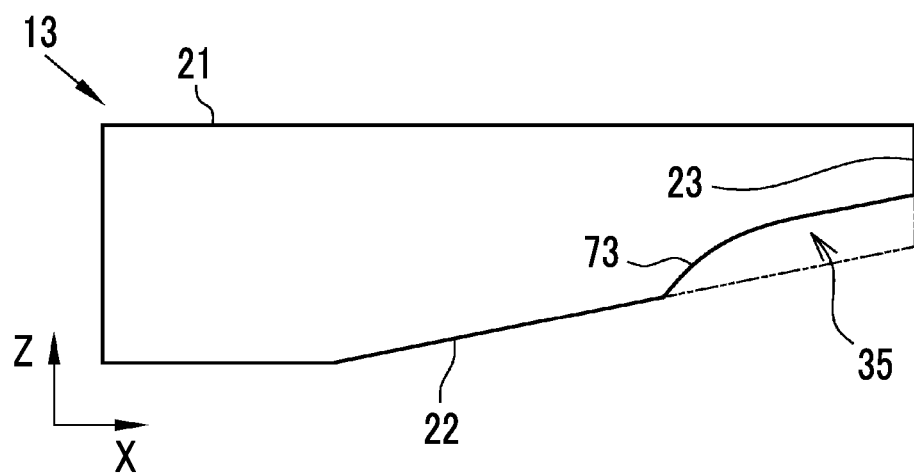

FIG. 12 is a diagram illustrating a modification example in which the recess is formed in a curved surface.

Figure 13:
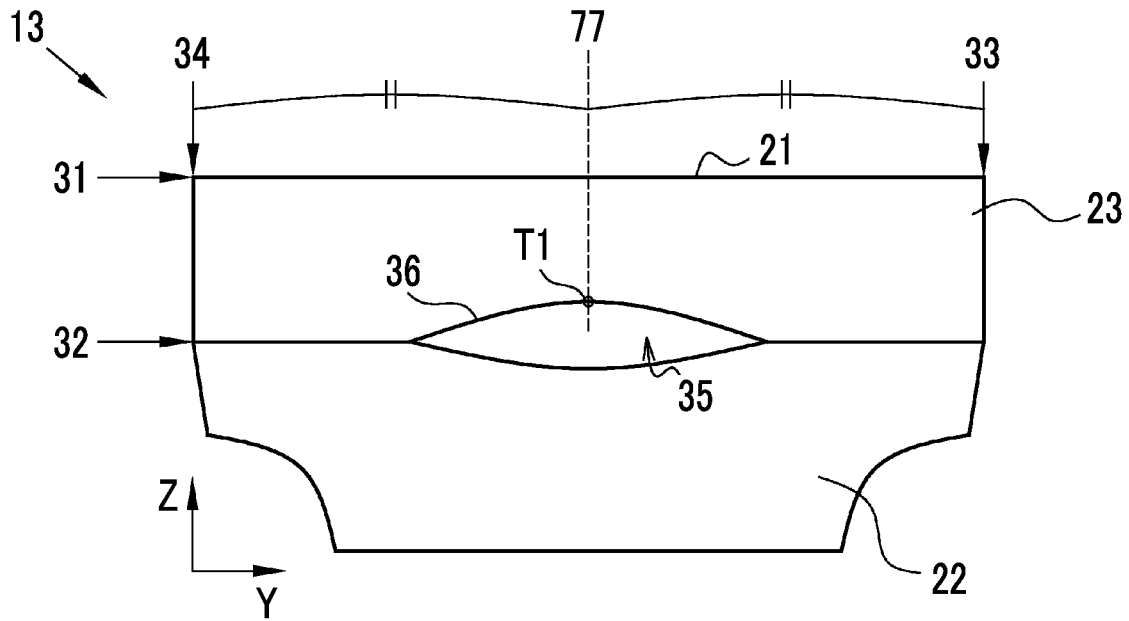

FIG. 13 is a diagram illustrating a position of a top of the recess.

Figure 14:
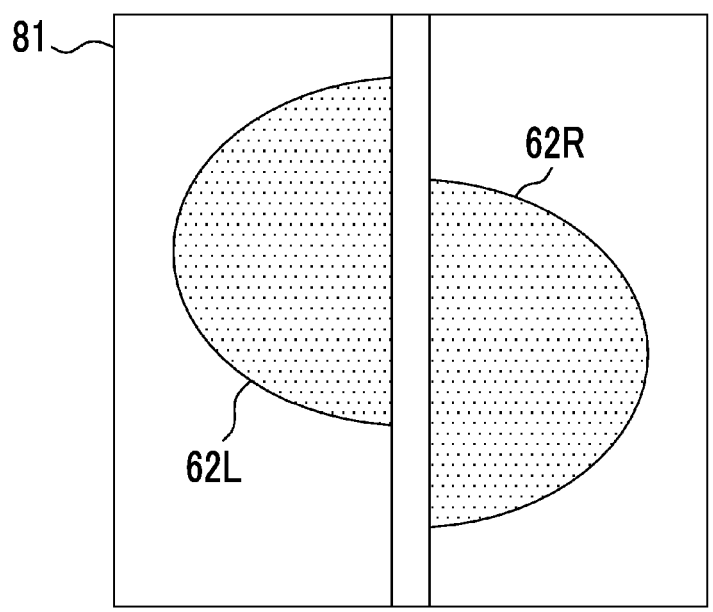

FIG. 14 shows a captured image before position adjustment.

Figure 15:
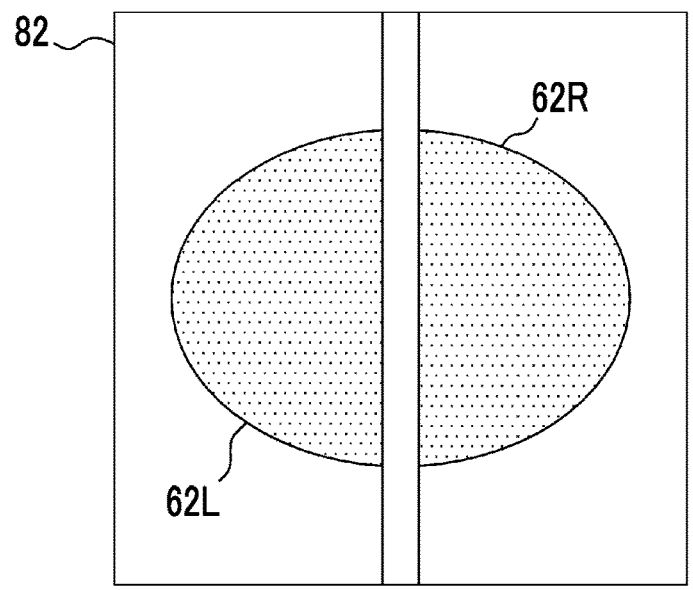

FIG. 15 shows a captured image after position adjustment.

Figure 16:
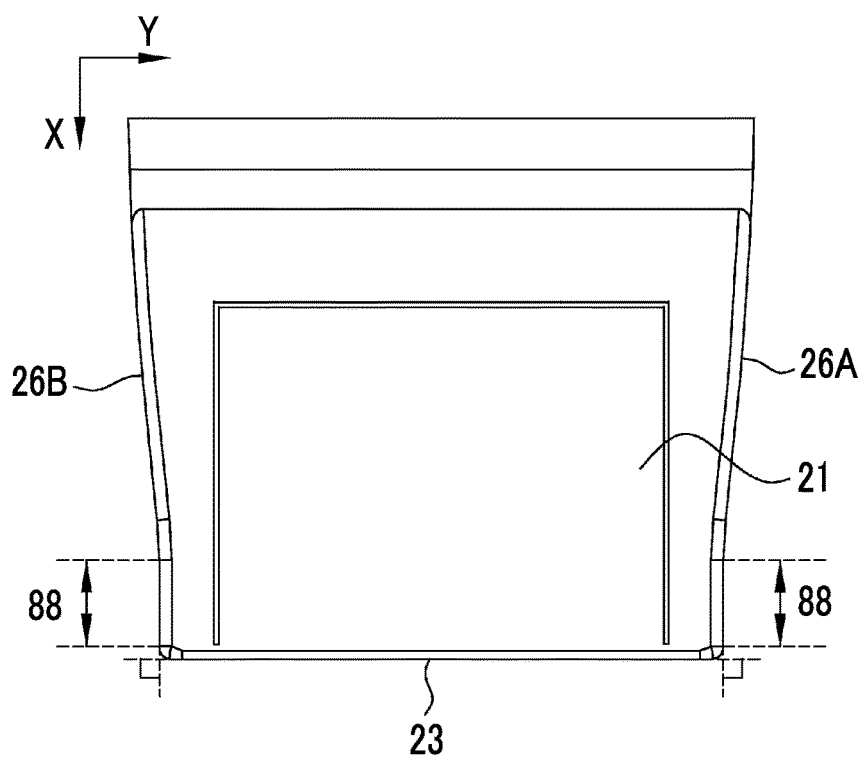

FIG. 16 is a plan view showing a straight portion of a first side face and a second side face.

Figure 17:
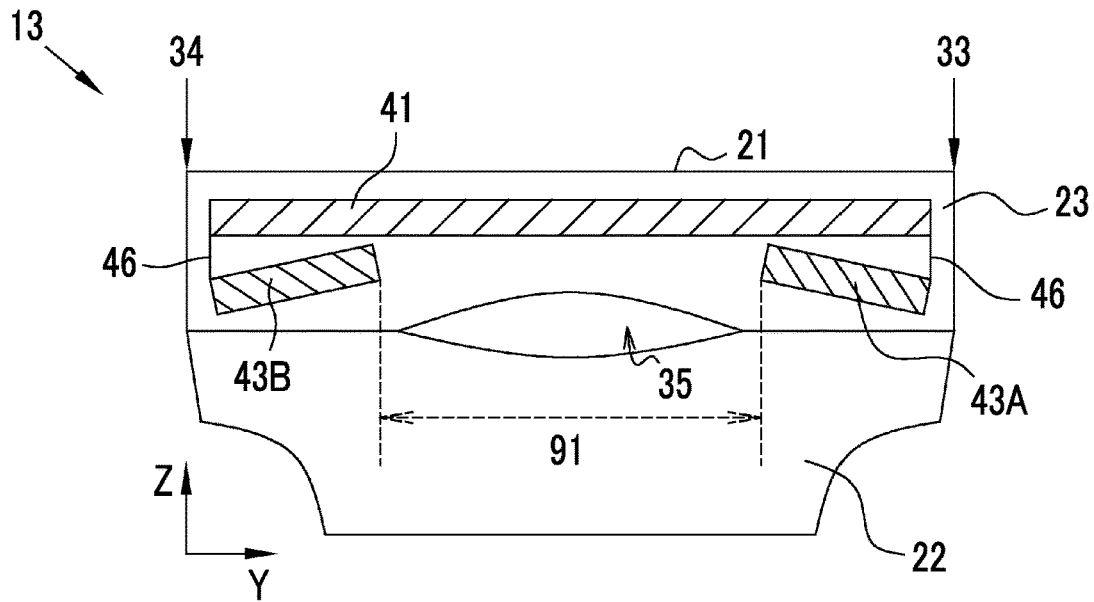

FIG. 17 is a diagram illustrating a modification example in which a control circuit is disposed to be tilted inside the imaging stand.

Figure 18:
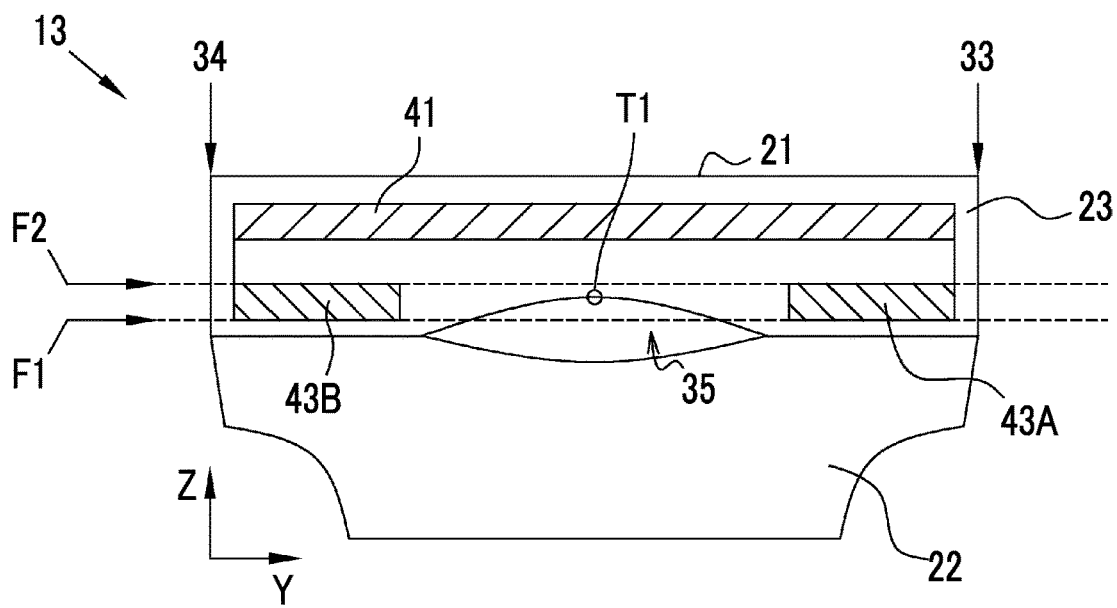

FIG. 18 is a diagram illustrating an appropriate position of the top of the recess on the contact face.

Figure 19:
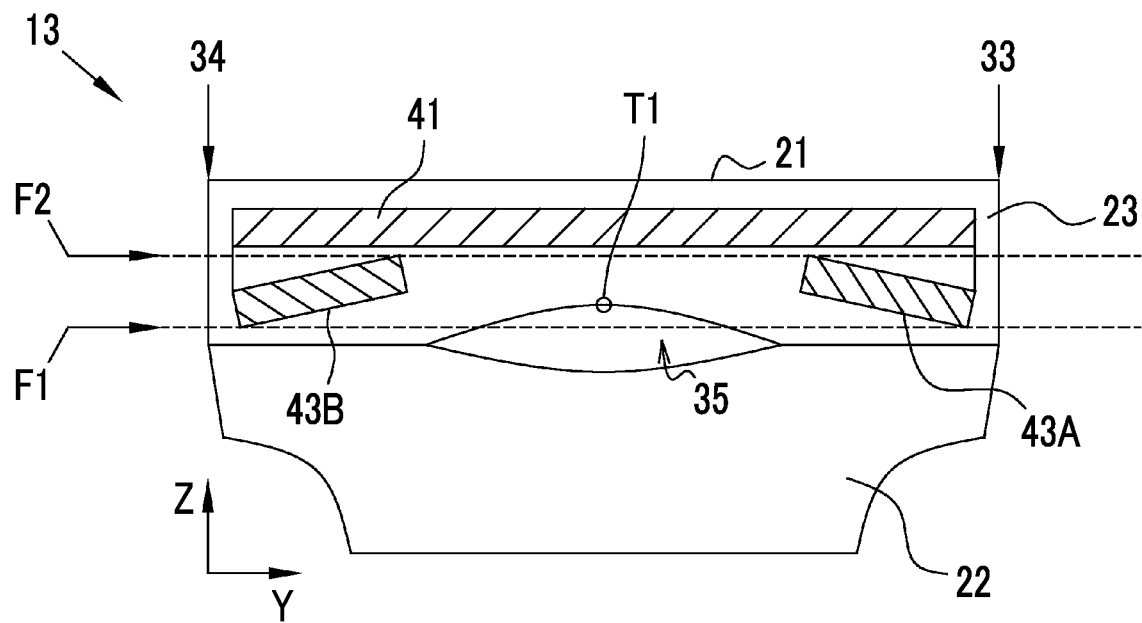

FIG. 19 is a diagram illustrating an appropriate position of the top of the recess on the contact face in a case where the control circuit is disposed to be tilted.

Figure 20:
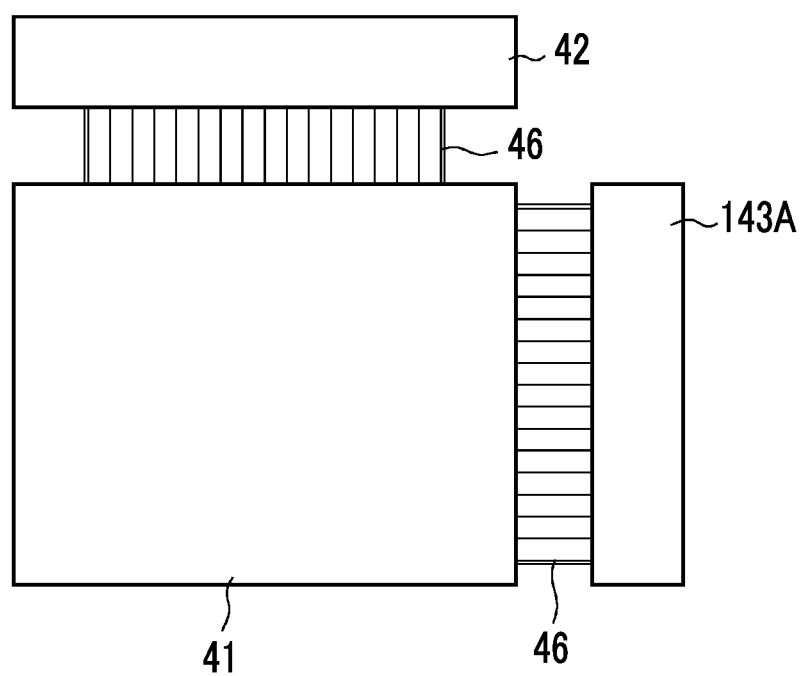

FIG. 20 is a diagram illustrating a disposition example of the control circuit in a case where one side reading is performed.

Figure 21:
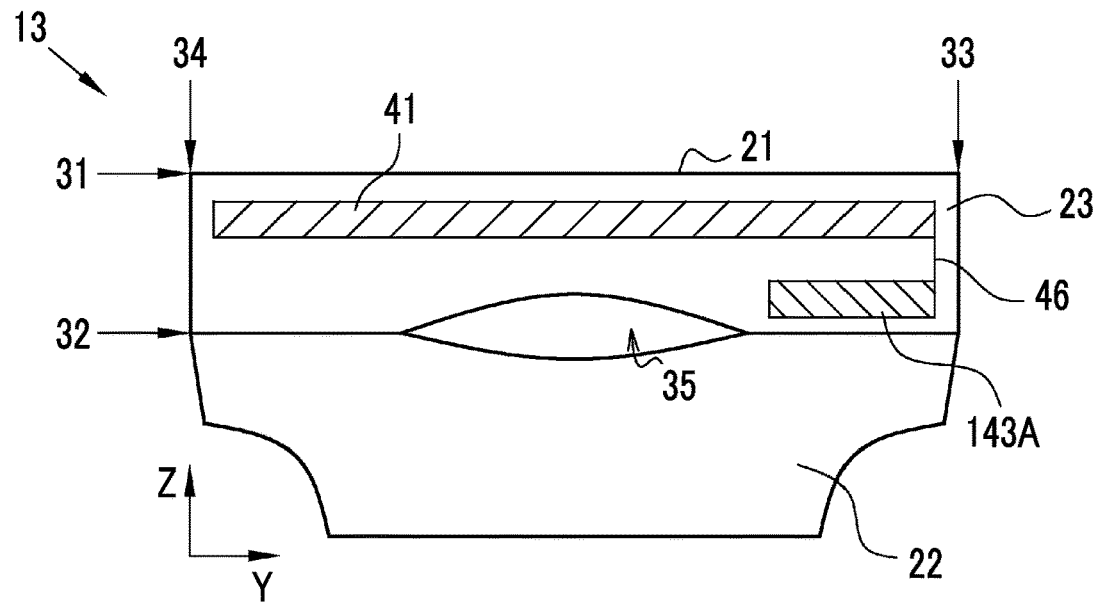

FIG. 21 is a diagram illustrating a disposition example of the control circuit in a case where the one side reading is performed.

Figure 22:
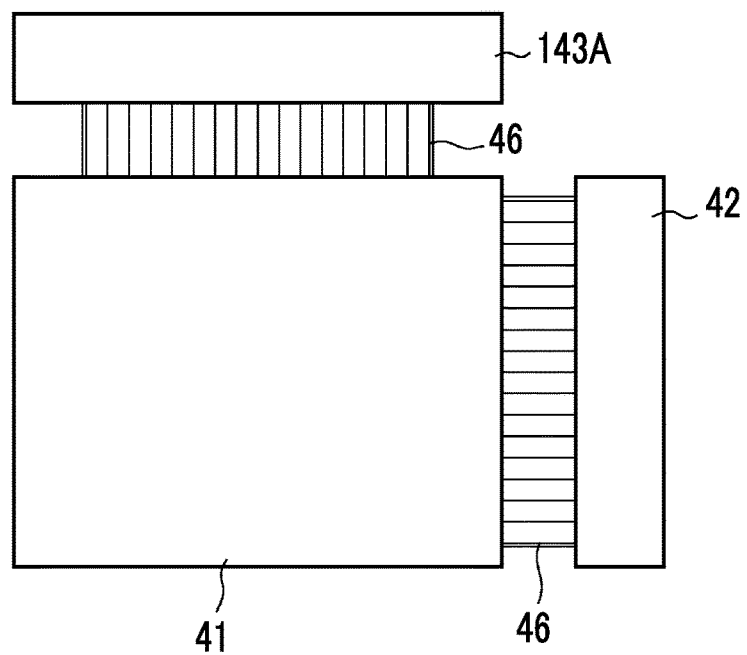

FIG. 22 is a diagram illustrating a disposition example of the control circuit in a case where the one side reading is performed.

Figure 23:
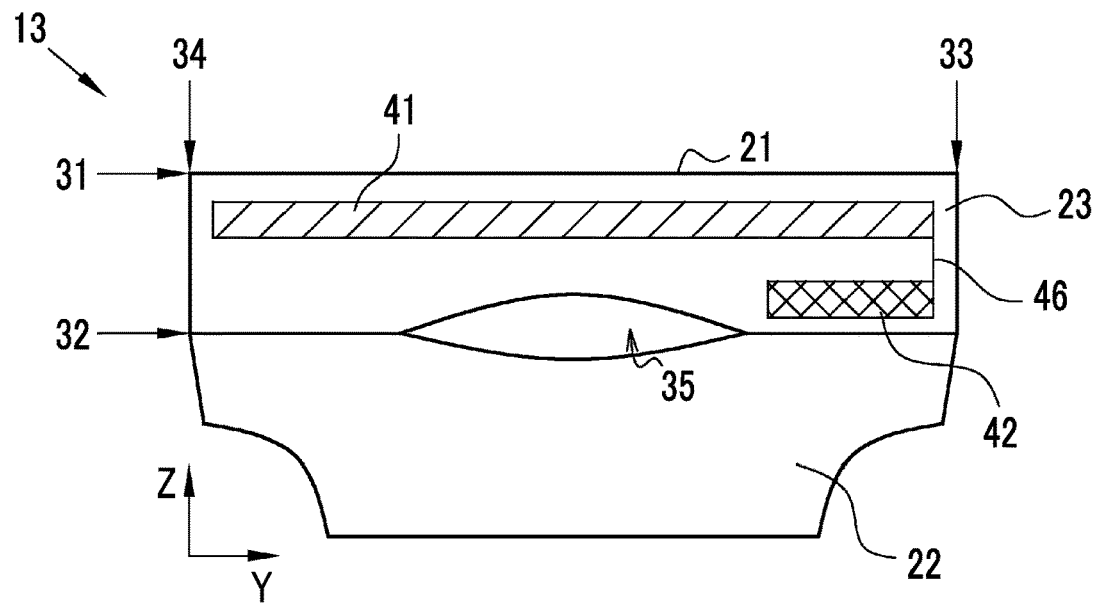

FIG. 23 is a diagram illustrating a disposition example of the control circuit in a case where the one side reading is performed.

Figure 24:
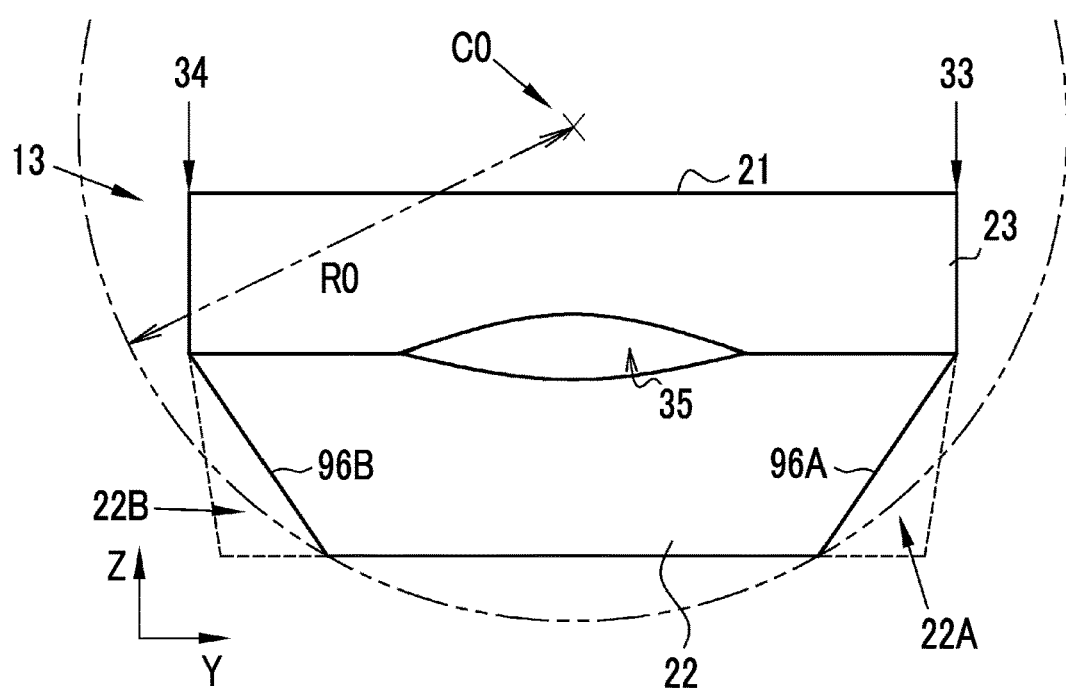

FIG. 24 is a diagram illustrating an example in which a part of the imaging stand is chamfered.

Figure 25:
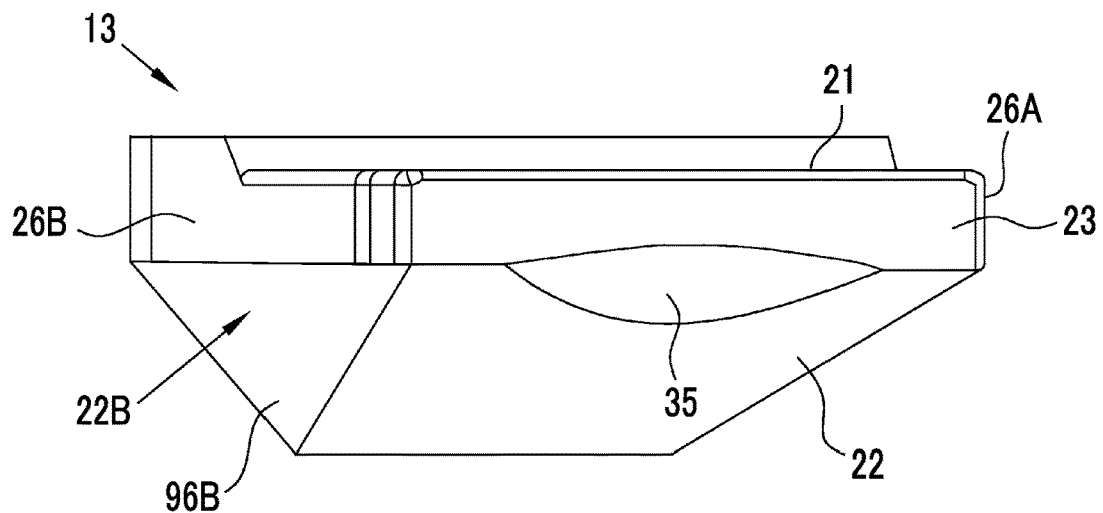

FIG. 25 is a perspective view showing an example in which a part of the imaging stand is chamfered.

Figure 26:
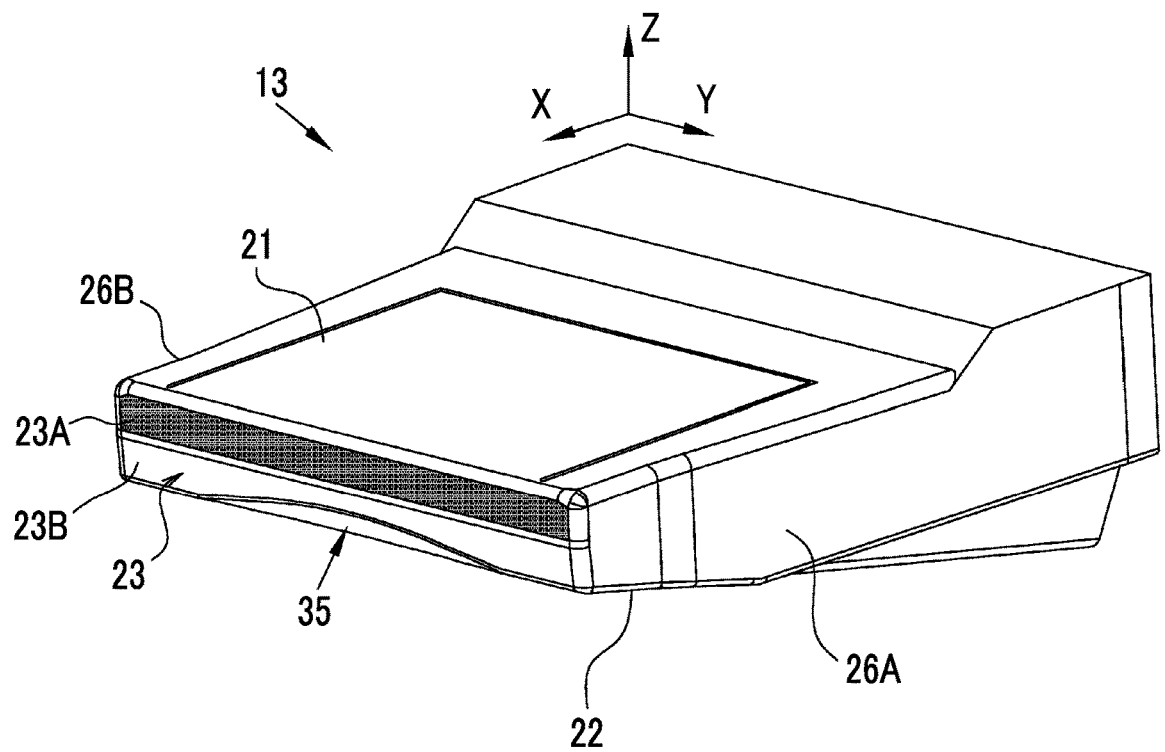

FIG. 26 is a perspective view showing the imaging stand in which the contact face is colored.

Figure 27:
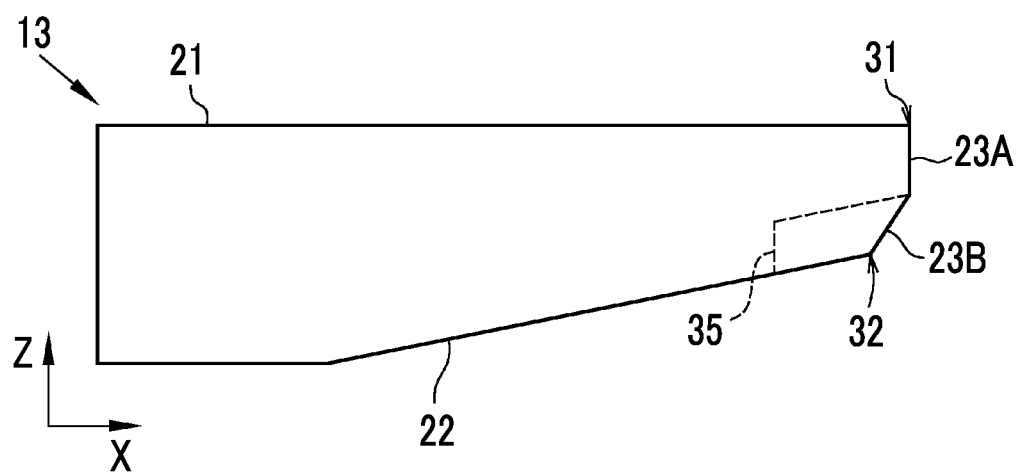

FIG. 27 is a diagram illustrating a modification example of a shape of the contact face.

DESCRIPTION OF THE PREFERRED EMBODIMENTS

First Embodiment

Figure 1:
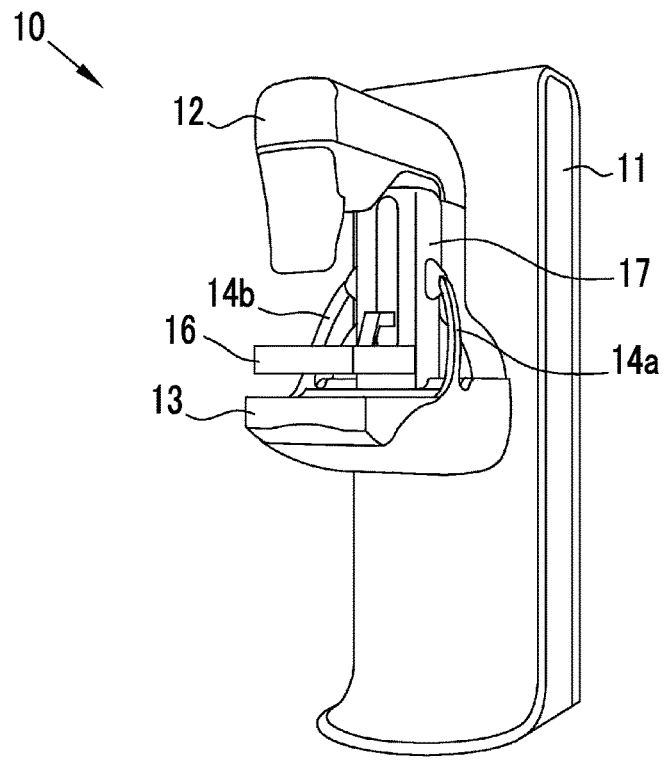
FIG. 1 is a perspective view of a mammography apparatus.

As shown in FIG. 1, a mammography apparatus 10 includes a column 11, an X-ray irradiation section 12, an imaging stand 13, a pressurizing plate 16, a lifting section 17, and the like. The mammography apparatus 10 is an X-ray imaging apparatus that images a breast of a subject 60 (see FIGS. 7 and 9) using X-rays. Further, the X-ray irradiation section 12 and the imaging stand 13 form an X-ray imaging unit.

The column 11 fixes the X-ray imaging unit or the like at a predetermined position in a predetermined direction on a floor face. The X-ray irradiation section 12 includes an X-ray tube that generates X-rays, and irradiates an X-ray imaging panel 41 (see FIG. 4) provided inside the imaging stand 13 with X-rays.

The imaging stand 13 is a stage on which a breast of the subject 60 is placed, and pinches a breast 62L or a breast 62R using the pressurizing plate 16 in imaging. Further, a grip portion 14a gripped by the right hand of the subject 60 and a grip portion 14b gripped by the left hand of the subject 60 are provided on the imaging stand 13. The grip portion 14a and the grip portion 14b are so-called armrests. Accordingly, by gripping the grip portion 14a or the grip portion 14b in imaging, the subject 60 puts the weight of arms or the like on the imaging stand 13 to easily maintain the posture of the subject 60.

The pressurizing plate 16 pressurizes the breast 62L or the breast 62R placed on the imaging stand 13 to make the breast 62L or the breast 62R flat. This is necessary to reduce overlapping of normal mammary glands and easily and definitely find out a lesion in a case where the lesion is present. The lifting section 17 lifts the pressurizing plate 16 with respect to the imaging stand 13. Thus, the lifting section 17 supports the pressurizing plate 16 to be almost flat with respect to the imaging stand 13, at a specific distance depending on the thickness of the breast 62L or the breast 62R.

As shown in (A) and (B) of FIG. 2, each section of the X-ray irradiation section 12, the imaging stand 13, and the like, which is attached to the column 11, is rotatable within a predetermined angle range while maintaining a relative position and a relative direction therebetween. Thus, the mammography apparatus 10 is able to perform imaging in a state where the imaging stand 13 is horizontally disposed or in a state where the imaging stand 13 is disposed to be tilted from the horizon. Specifically, as shown in (A) of FIG. 2, the mammography apparatus 10 is able to perform CC imaging for imaging a breast in a craniocaudal direction in a state where the imaging stand 13 is horizontally disposed. Further, as shown in (B) of FIG. 2, the mammography apparatus 10 is able to perform MLO imaging for imaging a breast in a mediolateral oblique direction in a state where the imaging stand 13 is disposed to be tilted. Although not shown, the mammography apparatus 10 may have a disposition in which the imaging stand 13 or the like is rotated in a direction opposite to the direction shown in (B) of FIG. 2.

As shown in FIG. 3, the imaging stand 13 includes an upper face 21, a lower face 22, a contact face 23, a first side face 26A, a second side face 26B, and a recess 35. Hereinafter, a side on which the upper face 21 is present is referred to as a Z-directional positive side, a side on which the lower face 22 is present is referred to as a Z-directional negative side, a side on which the contact face 23 is present is referred to as an X-directional positive side, a side on which the first side face 26A is present is referred to as a Y-directional positive side, and a side on which the second side face 26B is present is referred to as a Y-directional negative side. The imaging stand 13 is connected to the column 11 in a portion thereof on the X-directional negative side, and is rotated in an YZ in-plane direction with respect to the column 11. Further, it is assumed that, with respect to the imaging stand 13 or the respective portions (respective faces) that form the imaging stand 13, a "height" represents the length in the Z direction, a "width" represents the length in the Y direction, and a "depth" represents the length in the X direction.

The upper face 21 is a face on which a breast that is an imaging target is placed, and is a plane at least in a range where the breast is placed (a range where the X-ray imaging panel 41 is present). In this embodiment, the upper face 21 is relatively high on the side of the column 11 (X-directional negative side) further than the side of the contact face 23 (X-directional positive side), but this is because the control circuit or the like of the X-ray imaging panel 41 is provided therein. Hereinafter, unless otherwise mentioned, the upper face 21 of the imaging stand 13 represents a flat portion on the side of the contact face 23.

The lower face 22 is a surface that is opposite to the upper face 21 in the imaging stand 13. Here, "opposite" means that the lower face 22 is present on a side opposite to the upper face 21 in the shape of the imaging stand 13. In this embodiment, the upper face 21 and the lower face 22 are not parallel to each other, and the lower face 22 is tilted at a predetermined angle with reference to the upper face 21. The tilting of the lower face 22 is approximately constant. Here, an interval between the lower face 22 and the upper face 21 becomes small as it goes closer to the contact face 23, and an interval between the lower face 22 and the upper face 21 becomes large as it goes closer to the column 11.

The contact face 23 is a surface of the imaging stand 13 connected to the upper face 21 and the lower face 22, and is in contact with a chest wall of a subject 60 in imaging. Hereinafter, a portion where the contact face 23 and the upper face 21 are connected to each other is referred to as a first ridge portion 31 (ridge portion), and a portion where the contact face 23 and the lower face 22 are connected to each other is referred to as a second ridge portion 32 (ridge portion). Further, a portion where the contact face 23 and the first side face 26A are connected to each other is referred to as a third ridge portion 33, and a portion where the contact face 23 and the second side face 26B are connected to each other is referred to as a fourth ridge portion 34. The first ridge portion 31 is a portion of a ridgeline formed by the contact face 23 and the upper face 21. In this embodiment, a portion of a ridgeline formed by the contact face 23 and the upper face 21 is chamfered to form a curved surface. Accordingly, the entirety of the curved portion disposed between the contact face 23 and the upper face 21 corresponds to the first ridge portion 31. Similarly, the second ridge portion 32 is a portion of a ridgeline formed by the contact face 23 and the lower face 22, the third ridge portion 33 is a portion of a ridgeline formed by the contact face 23 and the first side face 26A, and the fourth ridge portion 34 is a portion of a ridgeline formed by the contact face 23 and the second side face 26B. In this embodiment, a portion of a ridgeline formed by the contact face 23 and the lower face 22, a portion of a ridgeline formed by the contact face 23 and the first side face 26A, and a portion of a ridgeline formed by the contact face 23 and the second side face 26B are respectively chamfered to form curved surfaces. Accordingly, the entirety of the curved portion disposed between the contact face 23 and the lower face 22 corresponds to the second ridge portion 32, the entirety of the curved portion disposed between the contact face 23 and the first side face 26A corresponds to the third ridge portion 33, and the entirety of the curved portion disposed between the contact face 23 and the second side face 26B corresponds to the fourth ridge portion 34.

The recess 35 is formed by cutting out at least a part of the contact face 23. Further, the recess 35 has a shape that at least a part of the second ridge portion 32 among the first ridge portion 31, the second ridge portion 32, the third ridge portion 33, and the fourth ridge portion 34 is cut out and the first ridge portion 31, the third ridge portion 33, and the fourth ridge portion 34 are not cut out. More specifically, the recess 35 is a portion that is generally recessed toward the inside of the imaging stand 13, and is in a range that includes at least a part or the entirety of the second ridge portion 32 and does not include the first ridge portion 31. Accordingly, a part or the entirety of the second ridge portion 32 is depressed by the recess 35, but there is no depression due to the recess 35 in the first ridge portion 31. Accordingly, a part of the contact face 23 is missing due to the presence of the recess 35, and the height of the contact face 23 in a range where the recess 35 is present is lower than the height in another portion of the contact face 23. Further, the recess 35 is present in a range that does not include the third ridge portion 33 and the fourth ridge portion 34. Accordingly, there is no defective portion due to the recess 35 in the third ridge portion 33 and the fourth ridge portion 34.

The recess 35 has a structure in which a part or the entirety of the second ridge portion 32 is chamfered using a flat surface and/or a curved surface. Accordingly, the recess 35 is a depression in the height direction (Z direction) of the imaging stand 13 with reference to the lower face 22, and also, is a depression in the depth direction (X direction) of the imaging stand 13 with reference to the contact face 23. Accordingly, the recess 35 has a shape that protrudes from the lower face 22 toward the upper face 21 in an YZ plane (for example, when looking at the contact face 23 in front), and has a shape that protrudes from the contact face 23 toward the column 11 in an XY plane (for example, when looking at the upper face 21 in front). Further, the recess 35 is a depression of the contact face 23. Similarly, the recess 35 is also a depression of the lower face 22.

In this embodiment, the recess 35 is present in a part of the second ridge portion 32 including the center of the second ridge portion 32. The center of the second ridge portion 32 represents a point where a distance from the first side face 26A to the point and a distance from the second side face 26B to the point are approximately the same on the second ridge portion 32. Further, in this embodiment, the recess 35 is formed in a curved surface that is convex toward the upper face 21. This is because positioning of the subject 60 is easily performed at a position of the recess 35. The "curved surface that is convex toward the upper face 21" means that a boundary line 36 between the recess 35 and the contact face 23 forms a convex curved surface toward the upper face 21 when looking at the imaging stand 13 from the contact face 23.

The direction of the imaging stand 13 is changed between a case where the CC imaging is performed and a case where the MLO imaging is performed, but since the imaging stand 13 is rotated in the YZ in-plane direction, the contact face 23 is in contact with the chest wall of the subject 60 even in any imaging.

The first side face 26A and the second side face 26B are surfaces of the imaging stand 13 that are connected to the upper face 21, the lower face 22, and the contact face 23. The first side face 26A is a side face of the imaging stand 13 in the Y-directional positive side. The second side face 26B is a side face of the imaging stand 13 in the Y-directional negative side.

As shown in FIG. 4, the imaging stand 13 includes the X-ray imaging panel 41, a switching circuit 42, a first reading circuit 43A, and a second reading circuit 43B.

The X-ray imaging panel 41 receives X-rays emitted by the X-ray irradiation section 12 to image a breast placed on the upper face 21. Thus, the mammography apparatus 10 obtains an X-ray image of the breast that is an imaging target. The X-ray imaging panel 41 is a so-called flat panel detector (FPD) that directly or indirectly converts X-rays into electric signals.

The switching circuit 42, the first reading circuit 43A, and the second reading circuit 43B are control circuits that control an operation of the X-ray imaging panel 41. In this embodiment, the first reading circuit 43A is a first control circuit, and the second reading circuit 43B is a second control circuit. The switching circuit 42 switches rows (or columns) of pixels for reading electric signals from the X-ray imaging panel 41. The first reading circuit 43A sequentially reads electric signals from pixels corresponding a half on the side of the first reading circuit 43A among the rows of the pixels designated by the switching circuit 42. The second reading circuit 43B sequentially reads electric signals from pixels corresponding a half on the side of the second reading circuit 43B among the rows of the pixels designated by the switching circuit 42. The X-ray imaging panel 41, and the switching circuit 42, the first reading circuit 43A and the second reading circuit 43B are connected to each other using, for example, a flexible board 46 (in which the flexible circuit board includes a simple cable, and is referred to as a flexible board). An integrated circuit or the like that performs signal processing, image processing, or the like may be mounted on the flexible board 46, as necessary.

Since the switching circuit 42, the first reading circuit 43A, and the second reading circuit 43B are connected to the X-ray imaging panel 41 using the flexible board 46, a part or the entirety thereof may be disposed on the lower face 22 side (hereinafter, referred to as a rear side) of the X-ray imaging panel 41 inside the imaging stand 13. In this embodiment, as shown in FIG. 5, both the first reading circuit 43A and the second reading circuit 43B are disposed to be folded on the rear side of the X-ray imaging panel 41. Further, the first reading circuit 43A is disposed on the side of the first side face 26A, and the second reading circuit 43B is disposed on the side of the second side face 26B. When looking at the imaging stand 13 from the contact face 23, the recess 35 is formed in a region 51 between the first reading circuit 43A and the second reading circuit 43B. This is a structure for providing the recess 35 without interference with the dispositions of the first reading circuit 43A and the second reading circuit 43B inside the imaging stand 13. The "between the first reading circuit 43A and the second reading circuit 43B" means "between a point of the first reading circuit 43A that is the closest to the second side face 26B to a point of the second reading circuit 43B that is the closest to the first side face 26A on the contact face 23 (when looking at the contact face 23 in front)". Further, the recess 35 is formed at least on the lower face 22 side of the X-ray imaging panel 41 when looking at the imaging stand 13 from the contact face 23. This is a structure for disposing the X-ray imaging panel 41 to be ultimately close to the contact face 23 that is in contact with a chest wall to enlarge an efficient imaging region.

As the first reading circuit 43A and the second reading circuit 43B are disposed on the rear side of the X-ray imaging panel 41, as shown in FIG. 6, the imaging stand 13 has a configuration in which an interval between the first side face 26A and the second side face 26B on the side of the contact face 23 (X-directional positive side) is narrower than that on the side of the column 11 (X-directional negative side). Accordingly, in the vicinity of the contact face 23 where the interval between the first side face 26A and the second side face 26B is narrow, the imaging stand 13 has a non-image region 49 of a small width (the length in the Y direction). The non-image region 49 is a region where an imaging face of the X-ray imaging panel 41 is not disposed, and thus, an X-ray image is not taken. In this embodiment, the width of the imaging stand 13 is about 360 mm, and the width of each of both the non-image regions 49 is about 30 mm. Further, in a portion of the imaging stand 13 on the side of the column 11, a support member (not shown) for connecting the imaging stand 13 to the column 11 and supporting the imaging stand 13 with respect to the column 11 is provided. Accordingly, the portion of the imaging stand 13 on the side of the column 11 has a wide interval between the first side face 26A and the second side face 26B further than that on the side of the contact face 23.

In this embodiment, the switching circuit 42 is disposed to be approximately parallel to the X-ray imaging panel 41, for example, on the side of the column 11 of the X-ray imaging panel 41. Further, the X-ray imaging panel 41 is disposed so that one side thereof approximately reaches the contact face 23.

In a case where the CC imaging is performed using the mammography apparatus 10 with such a configuration, as shown in FIG. 7, the imaging stand 13 is horizontally disposed, and the contact face 23 comes in contact with the chest wall 61 of the subject 60. Here, since the imaging stand 13 has the recess 35, the height of the contact face 23 in a portion that is actually in contact with the chest wall 61 of the subject 60 is smaller than the height of another portion of the contact face 23, the contact face 23 can be easily inserted between the breast 62R and the abdomen 63. Accordingly, compared with a related-art mammography apparatus that uses an imaging stand in which the recess 35 is not provided, the mammography apparatus 10 that uses the imaging stand 13 in which the recess 35 is provided can reduce stress applied to the subject 60 by pressing the abdomen 63 when the contact face 23 is in contact with the chest wall 61.

Further, it is necessary to maintain a state where the chest wall 61 of the subject 60 is in contact with the contact face 23 until imaging is terminated, but compared with a case where the recess 35 is not provided, in the imaging stand 13 in which the recess 35 is provided, since a part of the abdomen 63 is inserted into the recess 35, stress applied to the subject 60 as the imaging stand 13 pressurizes the abdomen 63 while the state where the contact face 23 is in contact with the chest wall 61 is maintained is reduced. The stress applied to the subject 60 in the CC imaging becomes large as the abdomen 63 becomes fat and big, but according to the imaging stand 13 in which the recess 35 is provided, even in a case where the abdomen 63 of the subject 60 is fat and big, it is possible to reduce stress generated by pressurization of the abdomen 63, for example.

In addition, since the imaging stand 13 is configured so that the recess 35 is provided in the second ridge portion 32 and is present in a range in which the recess 35 does not reach the first ridge portion 31 (particularly, on the lower face 22 side of the X-ray imaging panel 41), one side of the X-ray imaging panel 41 is approximately disposed on the contact face 23. Accordingly, as the contact face 23 is in contact with the chest wall 61 of the subject 60, it is possible to image almost the entirety of the breast 62R from the chest wall 61 into an X-ray image. For example, in a related-art mammography apparatus that uses an imaging stand having a shape that the contact face 23 is curved over the entirety thereof in the height direction between the upper face 21 and the lower face 22, it is necessary to dispose the position of the X-ray imaging panel 41 to shift toward the column 11 by a distance corresponding to a recess due to the curved portion of the contact face 23, and thus, an imaging range thereof is narrower than that of the imaging stand 13 in which the recess 35 is provided in the second ridge portion 32.

As shown in FIG. 8, since the imaging stand 13 is configured so that the recess 35 is provided in the second ridge portion 32, it is possible to set a height L2 of the first side face 26A and the second side face 26B on the contact face 23, irrespective of a distance L1 from a top T1 of the recess 35 to the upper face 21 (hereinafter, referred to as a minimum height of the contact face 23). The top T1 of the recess 35 refers to a top of the boundary line 36 between the recess 35 and the contact face 23. The minimum height L1 of the contact face 23 is, for example, 45 mm, and the height L2 of the first side face 26A and the second side face 26B is, for example, 60 mm. Accordingly, the height of the recess 35 on the contact face 23 is, for example, 15 mm.

The minimum height L1 of the contact face 23 is an optimal value obtained in consideration of an action relating to the shape of the recess 35 (for example, reduction in a pressurized feeling of the abdomen 63), heat dissipation of a heating part such as the X-ray imaging panel 41, difficulties in transmission of heat from the heating part such as the X-ray imaging panel 41 to the subject 60 through the recess 35, and difficulties in transmission of shock from the recess 35 or the like to a precision part such as the X-ray imaging panel 41. It is preferable that the minimum height L1 of the contact face 23 is equal to or smaller than 60 mm. With this configuration, it is possible to easily obtain an effect due to provision of the recess 35 even with respect to a plurality of subjects 60 with different physiques.

The height L2 of the first side face 26A and the second side face 26B is a height at which the subject 60 easily puts an arm on the first side face 26A or the second side face 26B in the MLO imaging. As shown in FIG. 9, in a case where the left breast 62L is subjected to the MLO imaging, the contact face 23 comes in contact to the chest wall 61 in a state where the imaging stand 13 is tilted. Here, the subject 60 can generally match, for example, the left shoulder 66L (or left armpit) with the ridge portion between the contact face 23 and the second side face 26B, and can put the left arm 67L and the left elbow 68L on the second side face 26B. Thus, the subject 60 can easily maintain the posture, and thus, compared with a case where an imaging stand on which the left arm 67L cannot be easily put on the second side face 26B is used, stress applied to the subject 60 in the MLO imaging is reduced. Then, the MLO imaging is performed in a state where the left breast 62L is put on the upper face 21 and is flatly pressurized using the pressurizing plate 16. This is similarly applied to a case where the right breast 62R is subjected to the MLO imaging.

As described above, in the MLO imaging, the reason why the arm or elbow is put on the first side face 26A or the second side face 26B to reduce the stress applied to the subject 60 is because the imaging stand 13 is configured so that the recess 35 is provided in the second ridge portion 32. That is, as the imaging stand 13 is configured so that the recess 35 is provided in the second ridge portion 32, it is possible to set the height L2 of the first side face 26A and the second side face 26B to a height at which the subject 60 easily puts the arm or the like in the MLO imaging, irrespective of the dimension of the recess 35.

For example, in a case where only stress due to pressurization from the imaging stand 13, for example, in the CC imaging is considered, a method for setting a portion of the contact face 23 of the imaging stand 13 together with the first side face 26A and the second side face 26B to be thin as much as possible, for example, to be equal to the thickness of the X-ray imaging panel 41 may be considered. However, in a case where the portion of the contact face 23 together with the first side face 26A and the second side face 26B is set to have a minimum thickness, it is not possible to secure the height L2 of the first side face 26A and the second side face 26B, and thus, it is difficult to put an arm or the like on the first side face 26A or the second side face 26B in the MLO imaging.

In the first embodiment, when looking at the imaging stand 13 from the contact face 23, a width W1 (see FIG. 8) of the recess 35 is, for example, 209 mm. This is about 70% of the width (300 mm) of the X-ray imaging panel 41 that is usually used in the mammography apparatus, which is a maximum dimension for preventing interference with the dispositions of the first reading circuit 43A and the second reading circuit 43B inside the imaging stand 13. The width of the X-ray imaging panel 41 refers to a length of an imaging surface formed with pixels that contribute to imaging in the X-ray imaging panel 41. Further, a width W2 (see FIG. 8) that is a distance from the recess 35 to the first side face 26A or the second side face 26B is, for example, 75.5 mm.

Preferably, the width W1 of the recess 35 is equal to or larger than about 45 mm, more preferably, equal to or larger than about 48 mm, and most preferably, equal to or larger than about 50 mm. In a case where the X-ray imaging panel 41 having at least a width of 300 mm is used, this is a minimum dimension at which the subject 60 easily senses an action of the recess 35. In a case where the width of the X-ray imaging panel 41 is used as a reference, preferably, the width W1 of the recess 35 is a length that is equal to or larger than about 15% of the width of the X-ray imaging panel 41, more preferably, a length that is equal to or larger than about 16%, and most preferably, a length that is equal to or larger than about 17%. This is a minimum dimension at which it is considered that the subject 60 easily senses the action of the recess 35 even in a case where the X-ray imaging panel 41 having a width different from that in the above description is used.

From the viewpoint of acquisition of the action due to provision of the recess 35, an upper limit of the width W1 of the recess 35 is the width of the contact face 23. That is, as long as the recess 35 does not interfere with the inside dispositions of the first reading circuit 43A, the second reading circuit 43B and the like, as shown in FIG. 10, the recess 35 may be substantially provided over the entirety of the second ridge portion 32. Here, preferably, the width W2 (see FIG. 8) that is the distance between the recess 35 and the first side face 26A or the second side face 26B is, for example, equal to or larger than 50 mm, more preferably, equal to or larger than 60 mm, and most preferably, equal to or larger than 75 mm. With this configuration, it is possible to easily secure a housing strength capable of withstanding the MLO imaging in which the arm or the like is put on the first side face 26A or the second side face 26B, even without considering a material and a thickness of the imaging stand 13.

In the first embodiment, the recess 35 is formed with a convex curved surface toward the upper face 21, but the recess 35 may be formed in a different shape. For example, as indicated by a boundary line 72 shown in FIG. 11, it is not essential that a boundary line between the recess 35 and the contact face 23 is a curve, and the boundary line may be formed with one or plurality of straight lines. Further, in the first embodiment, the recess 35 has clear edges (ridgelines) inside the recess 35 on the lower face 22 (see FIG. 7), but as shown in FIG. 12, the recess 35 may be formed with a curved surface 73 without clear edges on the lower face 22.

It is preferable that the ridge portion where the first side face 26A and the contact face 23 are connected to each other and the ridge portion where the second side face 26B and the contact face 23 are connected to each other are chamfered. Thus, in the MLO imaging, each of the ridge portions is smoothly and easily in contact with an armpit of the subject 60, and consequently, it is possible to reduce stress applied to the subject 60 in the MLO imaging. Similarly, it is particularly preferable that the ridge portion where the first side face 26A and the contact face 23 are connected to each other and the ridge portion where the second side face 26B and the contact face 23 are connected to each other are chamfered with curved surfaces. Further, in a case where the ridge portion where the first side face 26A and the contact face 23 are connected to each other and the ridge portion where the second side face 26B and the contact face 23 are connected to each other are chamfered with curved surfaces, it is preferable that a radius of curvature is large. It is preferable that the radius of curvature of the curved surfaces that forms the ridge portion where the first side face 26A and the contact face 23 are connected to each other and the ridge portion where the second side face 26B and the contact face 23 are connected to each other is equal to or larger than 3.5 mm, for example.

Second Embodiment

In the first embodiment, when seen from the contact face 23, it is sufficient if the shape of the recess 35 is convex toward the upper face 21, but it is preferable that not only the shape of the recess 35 is convex toward the upper face 21, but also, as shown in FIG. 13, the top T1 of the recess 35 (that is the top T1 of the boundary line 36 between the recess 35 and the contact face 23) is disposed nearly at the center between the first side face 26A and the second side face 26B. That is, it is preferable that the top T1 is disposed on a line 77 on which the distance from the first side face 26A and the distance from the second side face 26B are approximately the same, on the contact face 23. In this way, in a case where the top T1 of the recess 35 is disposed at the center between the first side face 26A and the second side face 26B, as the chest wall 61 is in contact with the contact face 23, the subject 60 is easily guided (so-called centering) to the center of the imaging stand 13. Accordingly, in a case where the CC imaging and the MLO imaging are respectively performed with respect to the left and right breasts 62L and 62R, the subject 60 is placed at an approximately determined position with respect to the imaging stand 13 in any imaging.

In breast cancer screening, one X-ray image in which respective images of the right breast 62R and the left breast 62L are laterally arranged from side to side is provided, but in a case where the imaging stand 13 does not have the recess 35, or in a case where the top T1 of the recess 35 excessively deviates from the center between the first side face 26A and the second side face 26B, the position of the subject 60 with respect to the imaging stand 13 is changed for each imaging, and thus, positions of images of the right and left breasts 62R and 62L normally shift from each other as indicated by an X-ray image 81 shown in FIG. 14. Accordingly, as shown in FIG. 15, an X-ray photographer generates an X-ray image 82 in which the positions of the right and left breasts 62R and 62L are adjusted, and provides the X-ray image 82 to a radiologist. On the other hand, in a case where the recess 35 is present in the imaging stand 13 and the top T1 of the recess 35 is disposed at approximately the center between the first side face 26A and the second side face 26B, since the subject 60 is placed at an approximately determined position with respect to the imaging stand 13, it is possible to easily obtain an X-ray image that is equivalent to the X-ray image 82 in which the positions of the right and left breasts 62R and 62L are adjusted.

Third Embodiment

In the first embodiment and the second embodiment, the shapes of the first side face 26A and the second side face 26B are nearly random, but as shown in FIG. 16, it is preferable that the first side face 26A and the second side face 26B include a straight portion 88 that crosses the contact face 23 at about 90 degrees, in at least a specific range from the contact face 23. In a case where the first side face 26A and the second side face 26B include the straight portion 88, the subject 60 can easily put an arm or the like on the first side face 26A or the second side face 26B in the MLO imaging. Specifically, there is a case where it is difficult for the subject 60 to raise the arm highly due to so-called frozen shoulder. However, even in the case of such a subject 60, in a case where the straight portion 88 is present in the first side face 26A and the second side face 26B, as long as the subject 60 can lift the arm and elbow up to about the height of the shoulder, it is possible for the subject 60 to put the arm and elbow on the first side face 26A and the second side face 26B. Further, after putting the arm and elbow on the first side face 26A and the second side face 26B, it is not necessary to continuously put excessive stress to the shoulder due to the presence of the straight portion 88, and thus, it is possible to enjoy imaging while holding the weight of the arm to the imaging stand 13. For example, in a case where the entirety of the first side face 26A and the second side face 26B are tilted toward the contact face 23 from the column 11, without the straight portion 88, it is necessary for the subject 60 to lift the arm and elbow up to the tilting angle, and thus, it is difficult to loosen tension of the shoulder in order to continuously put the arm and elbow on the first side face 26A and the second side face 26B.

The specific range is, for example, about 65 mm from the contact face 23. In a case where the straight portion 88 having such a length is provided, compared with a case where the straight portion 88 is not present, the subject 60 can easily put the arm and elbow on the first side face 26A and the second side face 26B, and can easily maintain the posture after putting the arm and elbow on the first side face 26A and the second side face 26B. Preferably, the specific range in which the straight portion 88 is provided is equal to or larger than 30 mm from the contact face 23, and more preferably, equal to or larger than 65 mm. Further, the specific range in which the straight portion 88 is provided has no upper limit, and the entirety of the first side face 26A and the second side face 26B may have the straight portion 88 as long as the internal disposition of the imaging stand 13 allows such a configuration.

Fourth Embodiment

In the first embodiment, the first reading circuit 43A and the second reading circuit 43B are disposed to be parallel to the upper face 21 and the X-ray imaging panel 41 inside the imaging stand 13, but control circuits such as the first reading circuit 43A and the second reading circuit 43B may be disposed to be tilted inside the imaging stand 13. Particularly, in a case where the control circuits such as the first reading circuit 43A and the second reading circuit 43B are disposed on the lower face 22 side of the X-ray imaging panel 41, it is preferable that the control circuits are provided so that an edge portion thereof on the side of the recess 35 is tilted toward the upper face 21, when looking at the imaging stand 13 from the contact face 23.

Specifically, as shown in FIG. 17, when looking at the imaging stand 13 from the contact face 23, by lifting an edge portion of the first reading circuit 43A on the side of the recess 35 toward the upper face 21, the edge portion on the side of the recess 35 is tilted to be close to the X-ray imaging panel 41, further than an edge portion to which the flexible board 46 is connected. Further, in the case of the second reading circuit 43B, by lifting the edge portion on the side of the recess 35 toward the upper face 21, the edge portion on the side of the recess 35 is tilted to be close to the X-ray imaging panel 41, further than an edge portion to which the flexible board 46 is connected.

In this way, in a case where the first reading circuit 43A and the second reading circuit 43B are disposed to be tilted inside the imaging stand 13, a region 91 between the first reading circuit 43A and the second reading circuit 43B may be enlarged further than the region 51 (see FIG. 5) between the first reading circuit 43A and the second reading circuit 43B in the first embodiment or the like. As a result, compared with a case where the first reading circuit 43A and the second reading circuit 43B are disposed to be parallel to the X-ray imaging panel 41 and the upper face 21 as in the first embodiment, it is possible to increase the size of the recess 35. As the size of the recess 35 becomes large, the imaging stand 13 less pressurizes the abdomen 63 of the subject 60 in the CC imaging, and thus, it is possible to reduce stress applied to the subject 60. Further, mounting parts such as connectors are present in the first reading circuit 43A and the second reading circuit 43B, but in a case where the first reading circuit 43A and the second reading circuit 43B are disposed to be tilted, there is a case where it is possible to make the thicknesses of the mounting parts thin.

In the fourth embodiment, both the first reading circuit 43A and the second reading circuit 43B are disposed to be tilted, but only one of the first reading circuit 43A or the second reading circuit 43B may be disposed to be tilted. Even in this case, a region between the first reading circuit 43A and the second reading circuit 43B when looking at the imaging stand 13 from the contact face 23 is set to be larger than that of the region 51 between the first reading circuit 43A and the second reading circuit 43B in the first embodiment.

Fifth Embodiment

As in the first to fourth embodiments, in a case where the control circuits such as the first reading circuit 43A and/or the second reading circuit 43B are disposed on the lower face 22 side (rear side) of the X-ray imaging panel 41, it is preferable that the recess 35 is more convex toward the upper face 21 than the control circuits when looking at the imaging stand 13 from the contact face 23. Specifically, as shown in FIG. 18, when looking at the imaging stand 13 from the contact face 23, the recess 35 is formed so that the top T1 that is the point of the recess 35 that is the closest to the upper face 21 is disposed to be close to the upper face 21 side further than a line F1 that passes through points of the first reading circuit 43A and the second reading circuit 43B that are the closest to the lower face 22 and is parallel to the upper face 21. That is, when looking at the imaging stand 13 from the contact face 23, the recess 35 is formed to have a size that the recess 35 is inserted between the first reading circuit 43A and the second reading circuit 43B. With this configuration, it is possible to compactly form the imaging stand 13 while obtaining the action of the recess 35. Further, since the height of the recess 35 becomes high compared with a case where the top T1 is present on the lower face 22 side further than the line F1, it is possible to easily obtain the action of the recess 35 in the subject 60 of any physique.

Further, when looking at the imaging stand 13 from the contact face 23, it is preferable that the recess 35 is formed so that the top T1 that is the point of the recess 35 that is the closest to the upper face 21 is disposed to be close to the lower face 22 side further than a line F2 that passes through points of the control circuits that are the closest to the upper face 21 and is disposed on the lower face 22 side in the X-ray imaging panel 41 and is parallel to the upper face 21. That is, it is preferable that the recess 35 is formed so that the top T1 is present between the line F1 and a line F2. As the top T1 is disposed on the upper face 21 side further than the line F1, it is possible to compactly form the imaging stand 13, and as the top T1 is disposed on the lower face 22 side further than the line F2, it is possible to secure a minimum heat dissipation space of the X-ray imaging panel 41 inside the imaging stand 13. Further, it is possible to make it difficult to transfer heat generated by the X-ray imaging panel 41 to the subject 60 through the recess 35, and to make it difficult to transfer shock due to contact of the subject 60, for example, to a precision part such as the X-ray imaging panel 41 through the recess 35.

As shown in FIG. 19, this is similarly applied to a case where the control circuits disposed on the lower face 22 of the X-ray imaging panel 41, such as the first reading circuit 43A and/or the second reading circuit 43B, are disposed to be tilted inside the imaging stand 13. In this case, an interval between the line F1 and the line F2 becomes larger than that in a case where the control circuits disposed on the lower face 22 side of the X-ray imaging panel 41 are disposed to be parallel to the X-ray imaging panel 41 and the upper face 21 (see FIG. 19). As a result, it is possible to form the recess 35 to be large compared with a case where the control circuits disposed on the lower face 22 side of the X-ray imaging panel 41 are disposed to be parallel to the X-ray imaging panel 41 and the upper face 21, and thus, it is possible to reduce stress applied to the subject 60 by reducing pressurization of the abdomen 63 due to the imaging stand 13 in the CC imaging.

In a case where the shape of the recess 35 does not have a convex curved surface on the upper face 21 (see FIG. 11), the top of the recess 35 is a set (line) of points that are disposed to be the closest to the upper face 21 in a boundary line between the contact face 23 and the recess 35. For example, in FIG. 11, the entirety of a portion parallel to the upper face 21 in the boundary line 72 corresponds to the top of the recess 35. This is similarly applied to the respective embodiments other than the fifth embodiment.

In the first to fifth embodiments, in order to read a signal from the X-ray imaging panel 41 at high speed, the imaging stand 13 is provided with two reading circuits of the first reading circuit 43A and the second reading circuit 43B to perform reading from both sides of the X-ray imaging panel 41, but the X-ray imaging panel 41 may be configured to perform so-called one side reading. That is, as shown in FIGS. 20 and 21, the imaging stand 13 may include a one side reading circuit 143A instead of the first reading circuit 43A and the second reading circuit 43B. In this case, similarly, conditions relating to the shape, position, size, and the like of the recess 35 are similar to those in the first to fifth embodiments.

In the case of the one side reading, as shown in FIGS. 22 and 23, a configuration in which the dispositions of the switching circuit 42 and the one side reading circuit 143A with respect to the imaging stand 13 and the X-ray imaging panel 41 are switched and the switching circuit 42 is disposed on the lower face 22 side of the X-ray imaging panel 41 may be used. Since the switching circuit 42 is the control circuit of the X-ray imaging panel 41, conditions relating to the shape, position, and size, and the like of the recess 35 are similar to those in the first to fifth embodiments.

Since the imaging stand 13 in the first to fifth embodiments and the imaging stand 13 in the modification example are rotated with respect to the column 11 for switching between the CC imaging and the MLO imaging, it is preferable that a part or the entirety of the surface of the imaging stand 13 is chamfered. Thus, in a case where the imaging stand 13 is rotated, it is possible to prevent the imaging stand 13 from colliding with a knee of the subject 60 or a car seat on which the subject 60 gets. As shown in FIG. 24, in a case where the X-ray imaging unit including the imaging stand 13 is rotated around a rotation center C0, for example, by removing a portion 22A and a portion 22B of the imaging stand 13, it is possible to reduce a radius of rotation R0, compared with a case where the portion 22A and the portion 22B are not removed (indicated by broken lines). In this case, as shown in FIG. 25, the lower face 22 and the first side face 26A are connected to each other, for example, through a flat surface 96A, and the lower face 22 and the second side face 26B are connected to each other through a flat surface 96B.

A method for performing the chamfering in consideration of the rotation of the imaging stand 13 as described above is not particularly limited. That is, the flat surface 96A and the flat surface 96B may be formed through the chamfering as described above, or a concave surface, a convex surface, a different curved surface, or a combination of a flat surface and a curved surface having predetermined sizes and predetermined shapes may be formed through the above-mentioned chamfering. Further, the chamfering performed in consideration of the rotation of the imaging stand 13 does not cover only the portions 22A and 22B that form the lower face 22 of the imaging stand 13, but may also reach the first side face 26A and the second side face 26B.

As shown in FIG. 26, it is preferable that the imaging stand 13 in the first to fifth embodiments and the imaging stand 13 in the modification example have a configuration in which a portion 23A of the contact face 23 on the upper face 21 side and the portion 23B of the contact face 23 on the lower face 22 side have different colors. In a case where the portion 23A of the contact face 23 on the upper face 21 side and the portion 23B of the contact face 23 on the lower face 22 side have different colors, the subject 60 can recognize the portion 23A of the contact face 23 on the upper face 21 side as the height (thickness) of the imaging stand 13. Accordingly, it is possible to reduce a mental pressure of the subject 60 at least in the CC imaging. For example, in a case where the upper face 21 of the imaging stand 13 is black, the portion 23A of the contact face 23 on the upper face 21 side may be set to the same black as that of the upper face 21, and the portion 23B of the contact face 23 on the lower face 22 side may be set to white.

The imaging stand 13 in the first to fifth embodiments and the imaging stand 13 in the modification example may have a configuration in which the contact face 23 is formed in a shape other than a single plane. For example, as shown in FIG. 27, a configuration in which the portion 23A of the contact face 23 on the upper face 21 side is formed as a plane that is approximately vertical to the upper face 21 and the portion 23B of the contact face 23 on the lower face 22 side is formed as a plane that is tilted with respect to the portion 23A may be used. Further, at least one of the portion 23A on the upper face 21 side or the portion 23B on the lower face 22 side may be formed in curved surfaces, or both of them may be formed in curved surfaces. In this way, in a case where the contact face 23 is formed in the shape other than the single plane, it is possible to reduce an area at which the contact face 23 actually comes into contact with the subject 60 in the CC imaging, for example, and consequently, it is possible to reduce stress applied to the subject 60.

EXPLANATION OF REFERENCES

10: mammography apparatus
11: column
12: X-ray irradiation section
13: imaging stand
14a, 14b: grip portion
16: pressurizing plate
17: lifting section
21: upper face
22: lower face
22A, 22B: portion of imaging stand
23: contact face
23A, 23B: portion of contact face
26A: first side face
26B: second side face
31: first ridge portion 32: second ridge portion
33: third ridge portion
34: fourth ridge portion
35: recess
36, 72: boundary line
41: X-ray imaging panel
42: switching circuit
43A: first reading circuit
43B: second reading circuit
46: flexible board
49: non-image region
51: region
60: subject
61: chest wall
62L, 62R: breast
63: abdomen
66L: left shoulder
67L: left arm
68L: left elbow
73: curved surface
77: line
81, 82: X-ray image
88: straight portion
91: region
96A, 96B: flat surface
143A: one side reading circuit
C0: rotation center
F1, F2: line
L1: minimum height of contact face
R0: radius of rotation
T1: top
W1, W2: width

What is claimed is:

1. A mammography apparatus comprising:
an X-ray irradiation section that irradiates an X-ray imaging panel with X-rays; and
an imaging stand that includes the X-ray imaging panel and a control circuit of the X-ray imaging panel, and is provided with an upper face on which a breast of a subject is placed, a lower face that is opposite to the upper face, a contact face that is connected to the upper face and the lower face and comes in contact with a chest wall of the subject, a first side face and a second side face that are connected to the upper face and the contact face, and a recess formed by cutting out at least a part of the contact face,
wherein the recess has a shape in which between a first ridge portion where the contact face and the upper face are connected to each other, and a second ridge portion where the contact face and the lower face are connected to each other, at least a part of the second ridge portion is cut out from the lower face, and an entirety of the first ridge portion is not cut out from the upper face,
wherein the second ridge portion has a curved surface that is convex toward the upper face when seen from the contact face.

2. The mammography apparatus according to claim 1, wherein the recess is present in a part of the second ridge portion including a center of the second ridge portion.

3. The mammography apparatus according to claim 1, wherein the recess has a structure in which the second ridge portion is chamfered.

4. The mammography apparatus according to claim 1, wherein the recess is formed in the curved surface.

5. The mammography apparatus according to claim 1, wherein a top of a boundary line between the recess and the contact face is disposed at a center of the second ridge portion between the first side face and the second side face, when seen from the contact face.

6. The mammography apparatus according to claim 1, wherein the recess is disposed on the lower face side of the X-ray imaging panel, when seen from the contact face.

7. The mammography apparatus according to claim 1, wherein a first control circuit disposed on the lower face side and the first side face side of the X-ray imaging panel and a second control circuit disposed on the lower face side and the second side face side of the X-ray imaging panel are provided as the control circuit, and
wherein the recess is disposed between the first control circuit and the second control circuit, when seen from the contact face.

8. The mammography apparatus according to claim 1, wherein the control circuit is disposed on the lower face side of the X-ray imaging panel, and
wherein the recess is convex toward the upper face further than the control circuit, when seen from the contact face.

9. The mammography apparatus according to claim 8, wherein a point of the recess that is the closest to the upper face side is disposed on the upper face side further than a line that passes through a point of the control circuit that is the closest to the lower face side and is parallel to the upper face, when seen from the contact face.

10. The mammography apparatus according to claim 8, wherein a point of the recess that is the closest to the upper face side is disposed between a line that passes through a point of the control circuit that is the closest to the lower face side and is parallel to the upper face and a line that passes through a point of the control circuit that is the closest to the upper face side and is parallel to the upper face, when seen from the contact face.

11. The mammography apparatus according to claim 1, wherein the control circuit is disposed on the lower face side of the X-ray imaging panel, and
wherein the control circuit is disposed so that an edge portion thereof on the side of the recess is tilted toward the upper face, when seen from the contact face.

12. The mammography apparatus according to claim 1, wherein the first side face and the second side face include a straight portion that crosses the contact face at 90 degrees, in at least a specific range from the contact face.

13. The mammography apparatus according to claim 1, wherein the recess in the contact face has a length that is equal to or larger than 15% of the X-ray imaging panel.

14. The mammography apparatus according to claim 1, wherein the X-ray imaging panel has a rectangular shape.

15. A mammography apparatus comprising:
an X-ray irradiation section that irradiates an X-ray imaging panel with X-rays; and
an imaging stand that comprises an upper face, a lower face, a contact face, a first side face and a second side face,
wherein the contact face is substantially orthogonal to the upper face, the first side face and the second side face, and the lower face is connected to the contact face, the first side face and the second side face,
wherein among a first ridge portion where the contact face and the upper face are connected to each other, a second ridge portion where the contact face and the lower face are connected to each other, a third ridge portion where the contact face and the first side face are connected to each other, and a fourth ridge portion where the contact face and the second side face are connected to each other, each of the first ridge portion, the third ridge portion and the fourth ridge portion is a substantially a straight line, wherein a part of the second ridge portion is cut out and recessed toward the upper face and in a direction away from the contact face into a concave shape.

* * * * *